United States Patent
Nakamura et al.

(10) Patent No.: US 7,521,710 B2
(45) Date of Patent: Apr. 21, 2009

(54) ORGANIC THIN FILM TRANSISTOR

(75) Inventors: Hiroaki Nakamura, Chiba (JP);
Masatoshi Saitou, Chiba (JP); Tetsuo Tsutsui, Fukuoka (JP); Takeshi Yasuda, Fukuoka (JP)

(73) Assignees: Idemitsu Kosan Co., Ltd., Tokyo (JP); Kyusyu University, Fukuoka-shi (JP)

( * ) Notice: Subject to any disclaimer, the term of this patent is extended or adjusted under 35 U.S.C. 154(b) by 57 days.

(21) Appl. No.: 11/369,862

(22) Filed: Mar. 8, 2006

(65) Prior Publication Data
US 2007/0187674 A1    Aug. 16, 2007

(30) Foreign Application Priority Data
Feb. 16, 2006    (JP)    .............. 2006-039683

(51) Int. Cl.
*H01L 51/30*    (2006.01)
(52) U.S. Cl. .................. 257/40; 257/E51.031
(58) Field of Classification Search ........... 257/40, 257/E51.024, E51.025, E51.027, E51.028, 257/E51.031; 438/99; 428/1.1–1.2; 252/299.61, 252/299.63, 299.65
See application file for complete search history.

(56) References Cited

U.S. PATENT DOCUMENTS

| | | | |
|---|---|---|---|
| 5,444,811 A * | 8/1995 | Yoshimura et al. .......... | 385/141 |
| 5,536,949 A | 7/1996 | Hosokawa et al. | |
| 5,912,473 A * | 6/1999 | Wakita et al. ................ | 257/40 |
| 6,224,787 B1* | 5/2001 | Hanna et al. ............. | 252/299.3 |
| 6,733,904 B2* | 5/2004 | Tao et al. ................... | 428/690 |
| 2004/0165806 A1 | 8/2004 | Zhou et al. | |
| 2005/0156161 A1* | 7/2005 | Hanna et al. ................. | 257/40 |
| 2006/0113526 A1* | 6/2006 | Hanna et al. ................. | 257/40 |

FOREIGN PATENT DOCUMENTS

| | | |
|---|---|---|
| DE | 693 33 840 T2 | 12/2005 |
| EP | 0 610 514 A1 | 8/1994 |
| EP | 1 569 286 A2 | 8/2005 |
| GB | 2 388 600 A | 11/2003 |
| JP | 11-204266 | 7/1999 |
| JP | 3-93796 | 10/2000 |

(Continued)

OTHER PUBLICATIONS

Gorjanc, T.C., et al., "Oligo-p-phenylenevinlene organic thin-film transistors with chemically modified dielectric surfaces", J. Vac. Sci. Technol. A 22(3), May/Jun. 2004.*

(Continued)

*Primary Examiner*—Douglas M Menz
*Assistant Examiner*—Matthew W Such
(74) *Attorney, Agent, or Firm*—Oblon, Spivak, McClelland, Maier & Neustadt, P.C.

(57) ABSTRACT

A thin film transistor comprising at least three terminals consisting of a gate electrode, a source electrode and a drain electrode; an insulator layer and an organic semiconductor layer on a substrate, which controls its electric current flowing between the source and the drain by applying a electric voltage across the gate electrode, wherein the organic semiconductor layer comprises a styryl derivative having a styryl structure expressed by $C_6H_5$—$CH$=$CH$—$C_6H_5$, or a distyryl structure expressed by $C_6H_5$—$CH$=$CH$—$C_6H_5$—$CH$=$CH$—$C_6H_5$ each without molecular weight distribution. The transistor has a fast response speed (driving speed), and further, achieves a large On/Off ratio getting an enhanced performance as a transistor.

8 Claims, 5 Drawing Sheets

FOREIGN PATENT DOCUMENTS

| | | |
|---|---|---|
| JP | 2004-2392 | 1/2004 |
| JP | 2004-6271 | 1/2004 |
| JP | 2005-89318 | 4/2005 |
| JP | 2005-244236 | 9/2005 |

OTHER PUBLICATIONS

Capelli, R., et al., "A potential J aggregate molecular system: crystal packing and optical properties of 4,4'-bis(2,3,4,5,6-pentafluorostyryl)stilbene", Synthetic Metals, 139 (2003) 909-912.*

Geens, W., et al. "Field-Effect Mobilities in Spin-Cast and Vacuum-Deposited PPV-Type Pentamers." Synthetic Metals, vol. 122 (2001): pp. 191-194.*

Drolet, N. et al. "2,7-Carbazolenevinylene-Based Oligomer Thin-Film Transistors: High Mobility Through Structural Ordering." Adv. Funct. Mater., vol. 15 (2005): pp. 1671-1682.*

Morin, J.-F., et al. "Syunthesis and Characterization of Electroactive and Photoactive 2,7-Carbazolenevinylene-Based Conjugated Oligomers and Polymers." Chem. Mater., vol. 16, (2004): pp. 4619-4626.*

Ndayikengurukiye, H., et al. "Alkoxylated p-Phenylenevinylene Oligomers: Synthesis and Spectroscopic and Electrochemical Properties." Tetrahedron, vol. 53, No. 40 (1997): pp. 13811-13828.*

* cited by examiner

Device A

Device B

Device C

Device D

ORGANIC THIN FILM TRANSISTOR

TECHNICAL FIELD

The present invention relates to an organic thin film transistor having an organic semiconductor layer. Particularly, the present invention relates to an organic thin film transistor comprising a compound having high mobility and capable of high-speed operation.

BACKGROUND ART

Thin film transistors (TFT) are broadly used as switching elements for display devices such as liquid crystal display, etc. A cross sectional structure of a typical conventional TFT is shown in FIG. 10. As shown in FIG. 10, TFT comprises a gate electrode and an insulator layer in this order on the substrate, and further, comprises a source electrode and a drain electrode formed above the insulator layer having a predetermined distance between them. Over the insulator layer exposing between the electrodes, a conventional semiconductor layer is formed having partial surfaces of each electrodes. In TFT with such a structure, the semiconductor layer forms a channel region and an electric current flowing between the source electrode and the drain electrode is controlled by a voltage applied to the gate electrode resultantly causing an On-Off operation.

Conventionally, TFTs were fabricated employing amorphous silicon or polycrystalline silicon, however, there were problems that making screens large in display devices or so with the use of TFTs is accompanied by significantly soaring in manufacturing cost because a chemical vapor deposition (CVD) equipment used for the preparation of TFTs employing the silicon is very expensive. Further, because a film-forming process of the amorphous silicon or the polycrystalline silicon is carried out under an extremely high temperature, causing a limitation in kinds of the material employable as a substrate for TFT, there was the problem that a lightweight polymer film substrate or so is unemployable.

For the purpose of overcoming such a problem, a TFT with the use of an organic substance replacing the amorphous silicon or the polycrystalline silicon is proposed. With regard to the film-forming process for fabricating a TFT employing organic substances, a vacuum vapor deposition process or a wet-coating process is well known. Those film-forming processes enable not only to realize making screens large in display devices while suppressing soaring in manufacturing cost but also to relatively reduce a process temperature required for film-forming. Accordingly, a practical use of the TFT employing an organic substance is highly expected because of an advantage in little limitation in a selection of material for a substrate and as a result, a large number of report about TFT employing an organic substance are published. Examples of the report include Non-Patent Literatures 1 to 19 below.

Further, with regard to the organic substance employable in an organic compound layer of TFT, a multimer such as conjugate polymer or thiophene (refer to Patent Literatures 1 to 5 below, etc.); metallophthalocyanine compound (refer to Patent Literature 6 below, etc.); or condensed aromatic hydrocarbon such as pentacene (refer to Patent Literatures 7 and 8 below, etc.) is used singly or as a mixture in combination with another compound each other. With regard to the materials of n-type FET, for example, Patent Literature 9 below discloses 1,4,5,8-naphthalenetetracarboxyldiunhydride (NTCDA), 11,11,12,12-tetracyanonaphth-2,6-quinodimethan (TCN-NQD), 1,4,5,8-naphthalenetetracarboxyldiimide (NTCDI), etc.; and Patent Literature 10 below discloses phthalocyanine fluoride. Additionally, although Non-patent Literature 16 teaches that oligophenylenevinylene exhibits transistor characteristic, it does not disclose at all what kind of structure oligophenylenevinylene has. Because a home page of Lucent Technologies in United States of America (http://www.lucent.com/press/0902/020925.bla.html) concludes that a person among the main authors of the Non-patent Literature 16 forged data and because Non-patent Literature 17 withdraws the content of Non-patent Literature 16, the present invention never gets any influence from Non-patent literature 16. Further, although Non-patent Literature 18 mentions about TFT property of soluble phenylenevinylene, its electron mobility is extremely as small as about $10^{-5}$ cm$^2$/Vs because it has a long-chain alkyl group in its center position. Furthermore, although Non-patent Literature 19 mentions about electron mobility of phenylenevinylenepolymer (poly-paraphenylenevinylene (PPV)), it is also so small as $10^{-4}$ cm$^2$/Vs that any practical performance is not achieved. Namely, because PPV being a high molecular compound has a long main chain structure, a turbulence in crystal structure induced from bending or molecular weight distribution of the main chain structure reduces electronic field-effect mobility to the small values. On the other hand, although Patent Literature 11 reports about a preparation of a TFT device by obliquely vapor depositing a liquid crystal compound, a TFT device having superior performance without depending upon the liquid crystal compound or upon a film-forming process such as the obliquely vapor deposition process was eagerly desired.

On the other hand, there is an organic electroluminescence (EL) device as a device similarly using an electric conduction. However, the organic EL device generally forces to feed charges by applying a strong electric field of $10^6$ V/cm or greater across a thickness direction of a ultra-thin film of 100 nm or thinner, whereas it is necessary for the organic TFT to feed charges for several μm or longer with high-speed under an electric field of $10^5$ V/cm or smaller and accordingly, an enhanced electric conductivity becomes necessary for the organic substance itself. Despite the above circumstances, the conventional compounds in the organic TFT had problems in fast response as transistor because its capability for moving electrons was poor, because a field-effect mobility of electron was small, and because response speed was slow. Further, On/Off ratio was also small. The above On/Off ratio is defined as a value obtained by dividing an amount of an electric current flowing between a source and a drain when some gate voltage is applied (On) by an amount of an electric current flowing there when any gate voltage is not applied (Off). A word "On electric current" usually means an amount of a (saturated) electric current at a time when the electric current between the source and the drain saturates while increasing the drain voltage.

Patent Literature 1: Japanese Unexamined Patent Application Laid-Open No. Hei 8-228034
Patent Literature 2: Japanese Unexamined Patent Application Laid-Open No. Hei 8-228035
Patent Literature 3: Japanese Unexamined Patent Application Laid-Open No. Hei 9-232589
Patent Literature 4: Japanese Unexamined Patent Application Laid-Open No. Hei 10-125924
Patent Literature 5: Japanese Unexamined Patent Application Laid-Open No. Hei 10-190001
Patent Literature 6: Japanese Unexamined Patent Application Laid-Open No. 2000-174277
Patent Literature 7: Japanese Unexamined Patent Application Laid-Open No. Hei 5-55568

Patent Literature 8: Japanese Unexamined Patent Application Laid-Open No. 2001-94107
Patent Literature 9: Japanese Unexamined Patent Application Laid-Open No. Hei 10-135481
Patent Literature 10: Japanese Unexamined Patent Application Laid-Open No. Hei 11-251601
Patent Literature 11: Japanese Unexamined Patent Application Laid-Open No. 2005-142233
Non-patent Literature 1: F. Ebisawa et al. Journal of Applied Physics, vol. 54, p 3255; 1983
Non-patent Literature 2: A. Assadi et al. Applied Physics Letter, vol. 53, p 195; 1988
Non-patent Literature 3: G. Guillaud et al. Chemical Physics Letter, vol. 167, p 503; 1990
Non-patent Literature 4: X. Peng et al. Applied Physics Letter, vol. 57, p 2013; 1990
Non-patent Literature 5: G. Horowitz et al. Synthetic Metals, vol. 41-43, p 1127; 1991
Non-patent Literature 6: S. Miyauchi et al. Synthetic Metals, vol. 41-43; 1991
Non-patent Literature 7: H. Fuchigami et al. Applied Physics Letter, vol. 63, p 1372; 1993
Non-patent Literature 8: H. Koezuka et al. Applied Physics Letter, vol. 62, p 1794; 1993
Non-patent Literature 9: F. Garnier et al. Science, vol. 265, p 1684; 1994
Non-patent Literature 10: A. R. Brown et al. Synthetic Metals, vol. 68, p 65; 1994
Non-patent Literature 11: A. Dodabalapur et al. Science, vol. 2568, p 270; 1995
Non-patent Literature 12: T. Sumimoto et al. Synthetic Metals, vol. 86, p 2259; 1997
Non-patent Literature 13: K. Kudo et al. Thin Solid Films, vol. 331, p 51; 1998
Non-patent Literature 14: K. Kudo et al. Synthetic Metals, vol. 102, p 900; 1999
Non-patent Literature 15: K. Kudo et al. Synthetic Metals, vol. 111-112, p 11; 2000
Non-patent Literature 16: Advanced Materials Vol. 13, No. 16, p 1273; 2001
Non-patent Literature 17: Advanced Materials Vol. 15, No. 6, p 478; 2003
Non-patent Literature 18: W. Geens et al. Synthetic Metals, Vol. 122, p 191; 2001
Non-patent Literature 19: Lay-Lay Chua et al. Nature, Vol. 434, March 10 issue, p 194; 2005

DISCLOSURE OF THE INVENTION

In order for overcoming the above problems, an object of the present invention is to provide an organic thin film transistor having a fast response speed (driving speed), and further, with a large On/Off ratio.

As a result of intensive researches and studies to achieve the above object by the present inventors, it was found that an employment of a styryl derivative with a specified structure having a styryl group ($-CH=CH-C_6H_5$) as a material for an organic semiconductor layer in an organic thin film transistor enables to speed up the response speed (driving speed) resultantly completing the present invention.

Namely, the present invention provides a thin film transistor comprising at least three terminals consisting of a gate electrode, a source electrode and a drain electrode; an insulator layer and a novel organic semiconductor layer on a substrate, which controls its electric current flowing between the source and the drain by applying a electric voltage across the gate electrode, wherein the organic semiconductor layer comprises a styryl derivative having a styryl structure expressed by $C_6H_5-CH=CH-C_6H_5$ and without molecular weight distribution. Further, the present invention also provides the thin film transistor wherein the organic semiconductor layer comprises a distyryl derivative having a distyryl structure expressed by $C_6H_5-CH=CH-C_6H_5-CH=CH-C_6H_5$ and without molecular weight distribution. Still further, the present invention also provides the thin film transistor wherein the organic semiconductor layer comprises a styryl compound represented by a general formula (a) which will be illustrated below.

The transistor became to have a fast response speed (driving speed), and further, achieved a large On/Off ratio getting an enhanced performance as a transistor.

PREFERRED EMBODIMENTS TO CARRY OUT THE INVENTION

Figure 1:
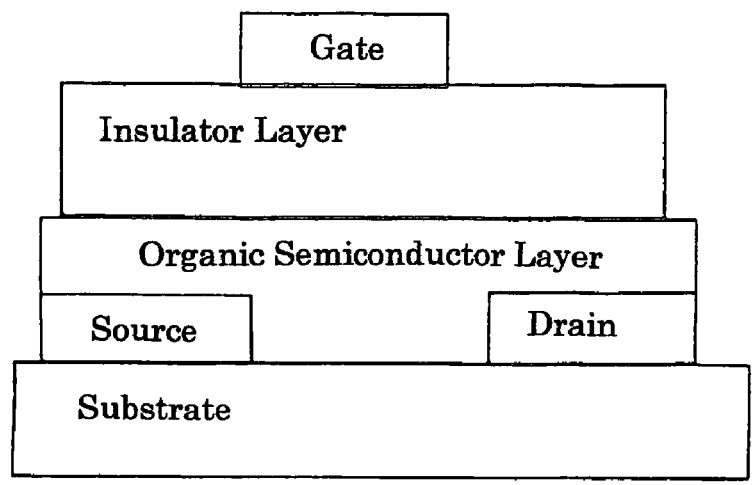
FIG. 1 is a drawing which illustrates one embodiment about device structure of an organic thin film transistor of the present invention.

The present invention provides a thin film transistor comprising at least three terminals consisting of a gate electrode, a source electrode and a drain electrode; an insulator layer and a novel organic semiconductor layer on a substrate, which controls its electric current flowing between the source and the drain by applying a electric voltage across the gate electrode, wherein the organic semiconductor layer comprises a styryl derivative having a styryl structure expressed by $C_6H_5-CH=CH-C_6H_5$ and without molecular weight distribution. Further, the present invention also provides the thin film transistor wherein the organic semiconductor layer comprises a distyryl derivative having a distyryl structure expressed by $C_6H_5-CH=CH-C_6H_5-CH=CH-C_6H_5$ and without molecular weight distribution.

The styryl structure of the styryl derivative in the present invention is defined as a structural unit shown in a following formula, that may have a substituent on a carbon atom composing this structure and further, the benzene ring portion may be a polycyclic condensed ring.

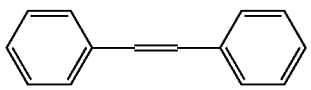

The distyryl structure of the distyryl derivative in the present invention is defined as a structural unit shown in a following formula which has a bonding style of continued benzene ring, olefin, benzene ring olefin and benzene ring wherein the structural unit may have a substituent on a carbon atom composing this structure and further, the benzene ring portion may be a polycyclic condensed ring. In the above structural unit, a steric position of olefin and a substituting position of benzene ring may be anywhere. The distyryl structure strengthens a mutual action between compounds and as a result, enables to obtain an enhanced current control characteristic.

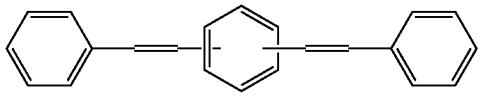

It is preferable that the distyryl structure has a following structure with a bonding position of two —CH═CH—C$_6$H$_5$ structure bonding to a central benzene ring each exists at para positions respectively.

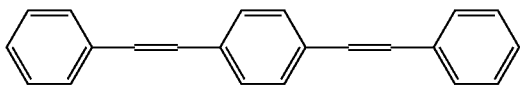

Further, the compound without molecular weight distribution in the present invention means the compound prepared aiming to control molecular weight in unity, and the compound may contain by-product in manufacture, impurity or additives for a certain object. On the contrary, a compound with molecular weight distribution means, a compound prepared by a manufacturing process in which the molecular weight cannot be controlled in unity such as, for example, a manufacturing process like polymerization, etc.

The foregoing styryl structure or distyryl structure, and the foregoing without having molecular weight distribution each improves crystallinity about film properties in thin film-formation of an organic semiconductor layer, resultantly enables to get superior films and enhanced current control characteristics.

It is preferable that the foregoing styryl derivative has at least the foregoing styryl structure and further, has a structure with arbitrary combinations of a unit structure selected from a group consisting of olefin, acetylene, aromatic hydrocarbon ring and aromatic heterocycle; wherein olefin and acetylene have bonding style between adjacent carbon atoms; and wherein aromatic hydrocarbon ring and aromatic heterocycle have bonding style bonding at a position not between adjacent elements. It is more preferable that the styryl derivative has at least the styryl structure and further, has a structure with arbitrary combinations of olefin or acetylene and aromatic hydrocarbon ring or aromatic heterocycle that bonds each other alternately.

Similarly, it is preferable that the foregoing distyryl derivative has at least the foregoing distyryl structure and further, has a structure with arbitrary combinations of a unit structure selected from a group consisting of olefin, acetylene, aromatic hydrocarbon ring and aromatic heterocycle; wherein olefin and acetylene have bonding style between adjacent carbon atoms; and wherein aromatic hydrocarbon ring and aromatic heterocycle have bonding style bonding at a position not between adjacent elements. It is more preferable that the distyryl derivative has at least the distyryl structure and further, has a structure with arbitrary combinations of olefin or acetylene and aromatic hydrocarbon ring or aromatic heterocycle that bonds each other alternately.

It is preferable that the above olefin has 2 to 8 carbon atoms. Examples include ethylene, propylene, butene, pentene, hexene, heptene, octene, etc. More preferable examples include ethylene, propylene and butene. Particularly preferable example is ethylene.

It is preferable that the above aromatic hydrocarbon ring has 6 to 30 carbon atoms. Examples include benzene, naphthalene, phenanthrene, anthracene, fluorene, perylene, pentacene and so on; each of which may be substituted.

It is preferable that the above aromatic heterocycle has 1 to 30 carbon atoms. Examples include furan, thiophene, pyrrole, pyrazole, imidazole, triazole, tetrazole, oxazole, isoxazole, thiazole, thiadiazole, pyridine, pyrimidine, benzofuran, benzothiophene, indole, quinoline, carbazole, dibenzofuran, dibenzothiophene and so on; each of which may be substituted.

Additionally, the phrase "olefin and acetylene have bonding style between adjacent carbon atoms" means the following bonding styles wherein X and Y each independently represents olefin, acetylene, aromatic hydrocarbon ring or aromatic heterocycle:

X—CH═CH—Y

X—C≡C—Y

Further, the phrase "aromatic hydrocarbon ring and aromatic heterocycle have bonding style bonding at a position not between adjacent elements" means the following bonding styles wherein X and Y each represents olefin, acetylene, aromatic hydrocarbon ring or aromatic heterocycle; and wherein a partial bonding structure is a single ring formula of 5-member ring or 6-member ring, a double rings formula of 5-member ring—5-member ring or 6-member ring—6-member ring.

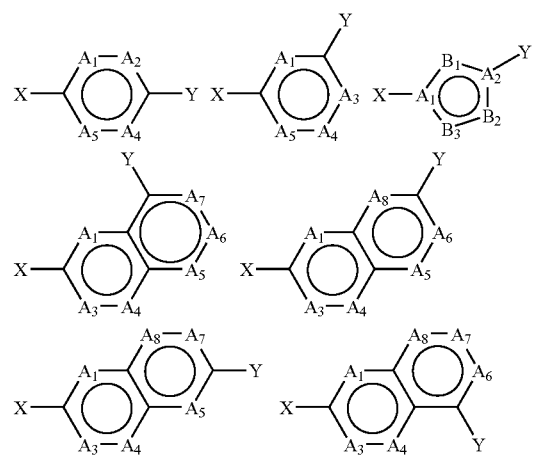

-continued

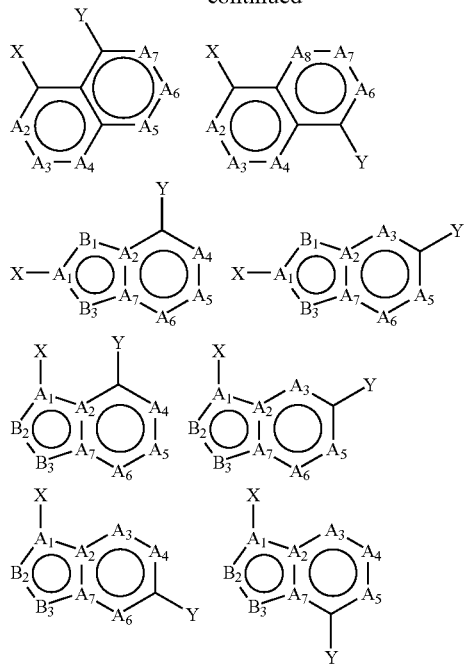

In the above bonding styles, $A_1$ to $A_8$ each independently represents a carbon atom or a nitrogen atom; $B_1$ to $B_3$ each independently represents a carbon atom, a nitrogen atom, an oxygen atom, a phosphorus atom or a sulfur atom and forms an aromatic hydrocarbon ring or a aromatic heterocycle. The aromatic hydrocarbon ring or the aromatic heterocycle is capable of having an arbitrary substituent which may form a ring structure with each other. When the arbitrary substituent of on the aromatic hydrocarbon ring or the aromatic heterocycle does not form a ring structure, a number of the carbon atoms, the nitrogen atoms, the oxygen atoms, the phosphorus atoms or the sulfur atoms each possessed by a main chain composing the substituent is preferably 10 or less, and further preferably 6 or less.

The foregoing bonding styles enable to control an alignment of molecules in compounds each other about the organic thin film transistor of the present invention, resultantly obtaining enhanced electric current control characteristics.

Furthermore, the phrase "a structure with arbitrary combinations of olefin or acetylene and aromatic hydrocarbon ring or aromatic heterocycle that bonds each other alternately" means a following repeating structure when the olefin or acetylene is expressed as $Z_1$ and the aromatic hydrocarbon ring or aromatic heterocycle is expressed as $Z_2$.

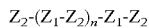

wherein n preferably represents an integer of 0 to 20.

The foregoing bonding styles enable to strengthen a mutual action between the compounds each other about the organic thin film transistor of the present invention, resultantly obtaining enhanced electric current control characteristics.

In the present invention, it is preferable that the styryl derivative or the distyryl derivative employed for the organic semiconductor layer is a styryl compound represented by a following general formula (a):

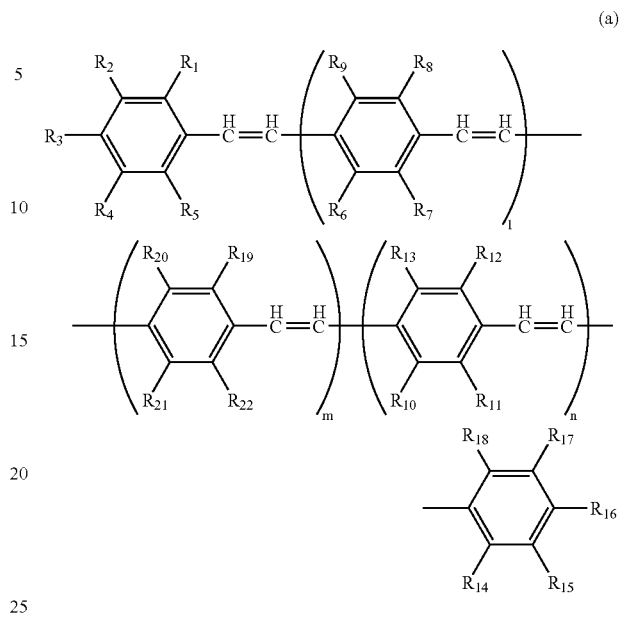

In the general formula (a), $R_1$ to $R_5$ and $R_{14}$ to $R_{18}$ each independently represents a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms and whose alkyl groups may bond each other to form a ring structure containing a nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, or an aromatic heterocyclic group having 1 to 60 carbon atoms, all of those may have a substituent.

In the general formula (a), $R_6$ to $R_{13}$ each independently represents a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms and whose alkyl groups may bond each other to form a ring structure containing a nitrogen atom, an alkylsulfonyl group having 1 to 30 carbon atoms, or a haloalkylsulfonyl group having 1 to 30 carbon atoms, all of those may have a substituent.

In the general formula (a), $R_{19}$ to $R_{22}$ each independently represents a hydrogen atom, a halogen atom, a cyano group, an alkyl group having 1 to 6 carbon atoms, a haloalkyl group having 1 to 6 carbon atoms, an alkoxyl group having 1 to 6 carbon atoms, a haloalkoxyl group having 1 to 6 carbon atoms, an alkylthio group having 1 to 6 carbon atoms, a haloalkylthio group having 1 to 6 carbon atoms, an alkylamino group having 1 to 6 carbon atoms, a dialkylamino group having 2 to 12 carbon atoms and whose alkyl groups may bond each other to form a ring structure containing a nitrogen atom, an alkylsulfonyl group having 1 to 6 carbon atoms, or a haloalkylsulfonyl group having 1 to 6 carbon atoms, all of those may have a substituent.

When the number of carbon atoms of the above $R_{19}$ to $R_{22}$ is within a range of from 1 to 6, a film property in the occasion of the thin film-formation never degrades and any reduction in its electric field-effect mobility or On/Off ratio never occurs.

In the general formula (a), l, m and n each independently represents an integer of 0 to 10, preferably 0 to 5.

In the general formula (a), a sum of l+m+n makes an integer of 0 to 20, preferably 1 to 20 and more preferably 1 to 10.

When the sum of l+m+n is 20 or smaller, a non-amorphous property of the film does not increase like polyphenylenevinylene high polymer, and any reduction in its electric field-effect mobility or On/Off ratio never occurs. Further in the general formula (a), although a steric structure of olefin part may mix each other, it is preferable that an essential component has a steric structure wherein a conjugated main chain is disposed in trans form.

In the general formula (a), it is preferable that $R_1$ to $R_{18}$ each independently represents a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms and whose alkyl groups may bond each other to form a ring structure containing a nitrogen atom, an alkylsulfonyl group having 1 to 30 carbon atoms, or a haloalkylsulfonyl group having 1 to 30 carbon atoms. Further, it is preferable that $R_{19}$ to $R_{22}$ each independently represents a hydrogen atom, a halogen atom, a cyano group, an alkyl group having 1 to 6 carbon atoms, a haloalkyl group having 1 to 6 carbon atoms, an alkoxyl group having 1 to 6 carbon atoms, a haloalkoxyl group having 1 to 6 carbon atoms, an alkylthio group having 1 to 6 carbon atoms, a haloalkylthio group having 1 to 6 carbon atoms, an alkylamino group having 1 to 6 carbon atoms, a dialkylamino group having 2 to 12 carbon atoms and whose alkyl groups may bond each other to form a ring structure containing a nitrogen atom, an alkylsulfonyl group having 1 to 6 carbon atoms, or a haloalkylsulfonyl group having 1 to 6 carbon atoms, all of those may have a substituent.

In the general formula (a), it is further more preferable that $R_6$ to $R_{13}$ and $R_{19}$ to $R_{22}$ each independently represents a hydrogen atom, a halogen atom, a cyano group, an alkyl group having 1 to 6 carbon atoms, or a haloalkyl group having 1 to 6 carbon atoms.

Further in the general formula (a), $R_3$ and $R_{16}$ each independently represents a hydrogen atom, a halogen atom, a cyano group, an alkyl group having 1 to 4 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms and whose alkyl groups may bond each other to form a ring structure containing a nitrogen atom, an alkylsulfonyl group having 1 to 30 carbon atoms, or a haloalkylsulfonyl group having 1 to 30 carbon atoms.

The above preferable selection of $R_3$ and $R_{16}$, and arranging the above number of carbon atoms to 30 or less will prevent a ratio of regularity control position of $R_3$ and $R_{16}$ occupying in the styryl compound of the general formula (a) from increasing too large, and will enable to control the regularity of the film because a density of phenylenevinylene skeleton contributing to current control, resultantly enabling to get high electric field-effect mobility and high On/Off ratio.

Still further in the general formula (a), it is preferable that $R_1$, $R_2$, $R_4$ to $R_{15}$ and $R_{17}$ to $R_{22}$ are all hydrogen atoms; at least one of $R_3$ or $R_{16}$ is an alkyl group having 1 to 3 carbon atoms, an alkoxyl group having 1 to 3 carbon atoms, or a hydrogen atom. It is more preferable that any one of $R_1$ to $R_{22}$ represents a fluorine atom, a trifluoromethyl group or a pentafluoropropyl group.

Furthermore, the compound with the styryl structure or the distyryl structure employed for the organic thin film transistor of the present invention has ambipolar transport property exhibiting p-type (hole conduction) and n-type (electron conduction), and the TFT can be driven as p-type device or as n-type device according to a combination of the source electrode and the drain electrode. However, an appropriate selection of the foregoing $R_1$ to $R_{22}$ in the general formula (a) depending on its necessity enables to enhance capabilities as p-type and n-type. In other words, an employment of a group with electron-accepting property for $R_1$ to $R_{22}$ reduces a level of Lowest Unoccupied Molecular Orbital (LUMO) and enables to work as a n-type semiconductor. Preferable examples of the group with electron-accepting property include hydrogen atom, halogen atom, cyano group, haloalkyl group having 1 to 30 carbon atoms, haloalkoxyl group having 1 to 30 carbon atoms, haloalkyl thio group having 1 to 30 carbon atoms and haloalkylsulfonyl group having 1 to 30 carbon atoms. Further, an employment of a group with electron-donating property for $R_1$ to $R_{22}$ enhances a level of Highest Occupied Molecular Orbital (HOMO) and enables to work as a p-type semiconductor. Preferable examples of the group with electron-donating property include hydrogen atom, alkyl group having 1 to 30 carbon atoms, alkoxyl group having 1 to 30 carbon atoms, alkylthio group having 1 to 30 carbon atoms, alkylamino group having 1 to 30 carbon atoms and dialkylamino group having 2 to 60 carbon atoms, in which alkyl group may bond each other to form a ring structure.

Specific examples of the each group represented by $R_1$ to $R_{22}$ in the general formula (a) will be explained below.

Examples of halogen atom include fluorine atom, chlorine atom, bromine atom and iodine atom.

Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, etc. Examples of the haloalkyl group include chloromethyl group, 1-chloroethyl group, 2-chloroethyl group, 2-chloro isobutyl group, 1,2-dichloroethyl group, 1,3-dichloro isopropyl group, 2,3-dichloro-t-butyl group, 1,2,3-trichloro propyl group, bromomethyl group, 1-bromoethyl group, 2-bromoethyl group, 2-bromo isobutyl group, 1,2-dibromo ethyl group, 1,3-dibromo isopropyl group, 2,3-dibromo-t-butyl group, 1,2,3-tribromo propyl group, iodomethyl group, 1-iodo ethyl group, 2-iodo ethyl group, 2-iodo isobutyl group, 1,2-diiodo ethyl group, 1,3-diiodo isopropyl group, 2,3-diiodo-t-butyl group, 1,2,3-triiodopropyl group, fluoromethyl group, 1-fluoromethyl group, 2-fluoromethyl group, 2-fluoro isobutyl group, 1,2-diphloloethyl group, difluoromethyl group, trifluoromethyl group, pentafluoro ethyl group, perfluoro isopropyl group, perfluorobutyl group, perfluorocyclohexyl group, etc.

The above alkoxyl group is a group expressed by $-OX^1$, and examples of $X^1$ are the same as those explained about the above alkyl group. The above haloalkoxyl group is a group expressed by $-OX^2$, and examples of $X^2$ are the same as those explained about the above haloalkyl group.

The above alkylthio group is a group expressed by —SX$^1$, and examples of X$^1$ are the same as those explained about the above alkyl group. The above haloalkoxyl group is a group expressed by —SX$^2$, and examples of X$^2$ are the same as those explained about the above haloalkyl group.

The above alkylamino group is a group expressed by —NHX$^1$, and the above dialkylamino group is a group expressed by —NX$^1$X$^3$, and examples of X$^1$ and X$^3$ are the same as explained about the above alkyl group respectively. Additionally, the alkyl group in the dialkylamino group may bond each other to form a ring structure having a nitrogen atom, and examples of the ring structure include pyrrolidine, piperidine, etc.

The alkylsulfonyl group is a group expressed by —SO$_2$X$^1$, and examples of X$^1$ are the same as those explained about the above alkyl group. The above haloalkylsulfonyl group is a group expressed by —SO$_2$X$^2$, and examples of X$^2$ are the same as those explained about the above haloalkyl group.

Examples of the above aromatic hydrocarbon group include phenyl group, naphthyl group, anthryl group, phenanthryl group, fluorenyl group, perilenyl group, pentacenyl group, etc. Examples of the aromatic heterocyclic group include furanyl group, thiophenyl group, pyrrolyl group, pyrazolyl group, imidazolyl group, triazolyl group, tetrazolyl group, oxazolyl group, isoxazolyl group, thiazolyl group, thiadiazolyl group, pyridinyl group, pyrimidinyl group, benzofuranyl group, benzthiophenyl group, indolyl group, quinolinyl group, carbazolyl group, dibenzofuranyl group, dibenzothiophenyl group, etc.

Examples of a substituent that may be further substituted to each groups represented in the foregoing general formula (a) include aromatic hydrocarbon group, aromatic heterocyclic group, alkyl group, alkoxy group, aralkyl group, aryloxy group, arylthio group, alkoxycarbonyl group, amino group, halogen atom, cyano group, nitro group, hydroxyl group, carboxyl group, etc.

Specific examples of the styryl derivative, distyryl derivative and the styryl compound represented by the general formula (a) all employable for the organic semiconductor layer of the organic thin film transistor of the present invention will be shown below, though not particularly limited thereto.

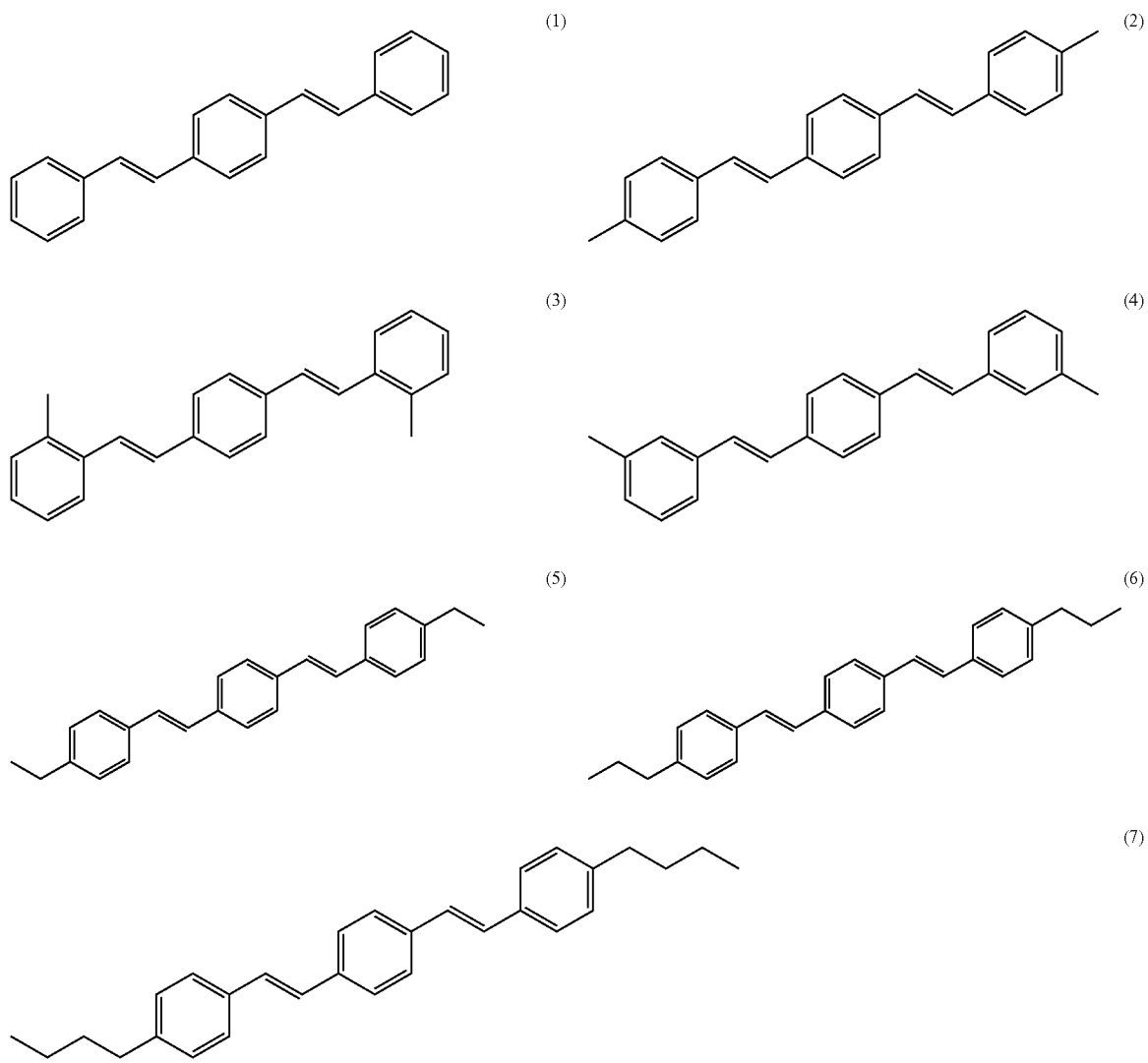

-continued
(8)
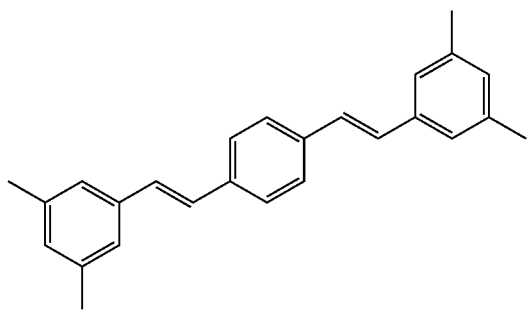
(9)
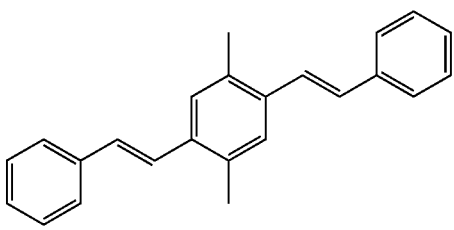
(10)
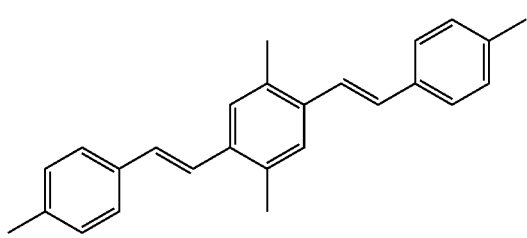
(11)
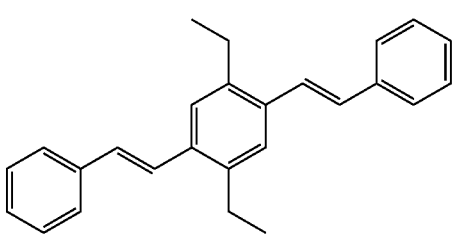
(12)
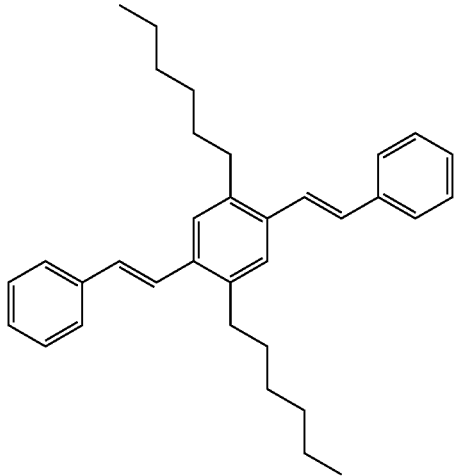
(13)
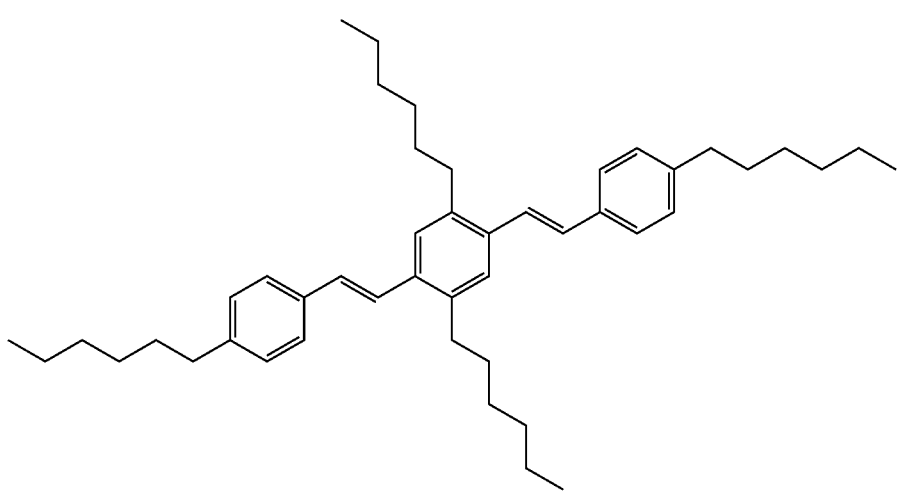

-continued
(14)
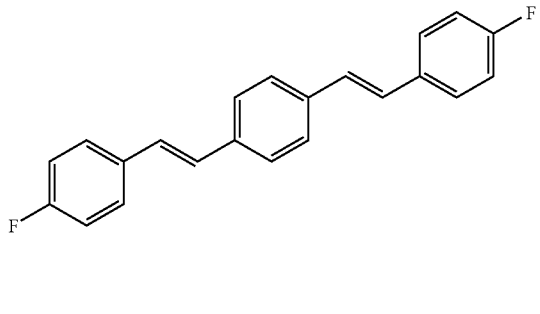
(15)
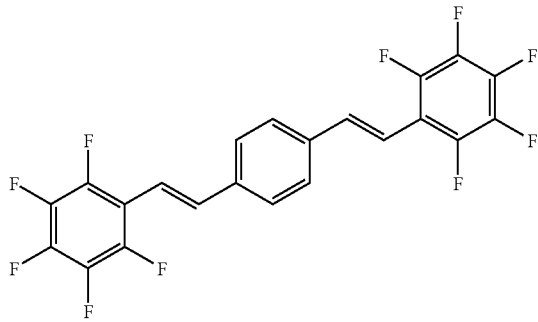
(16)
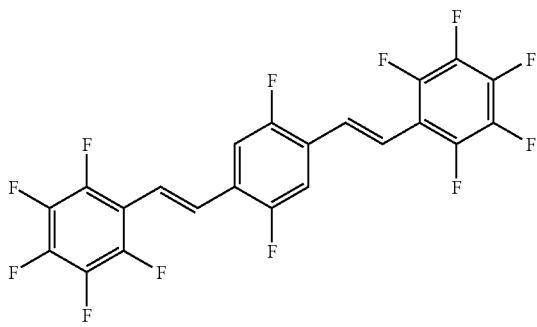
(17)
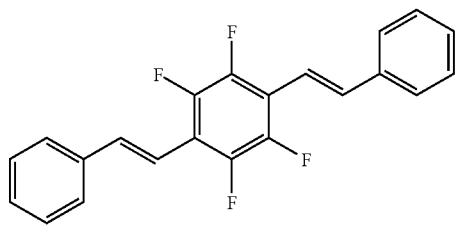
(18)
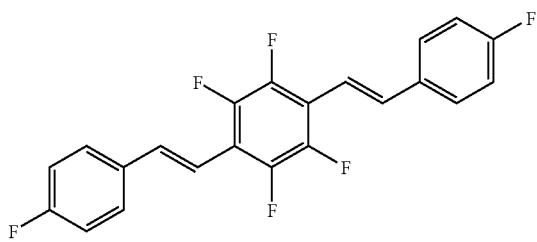
(19)
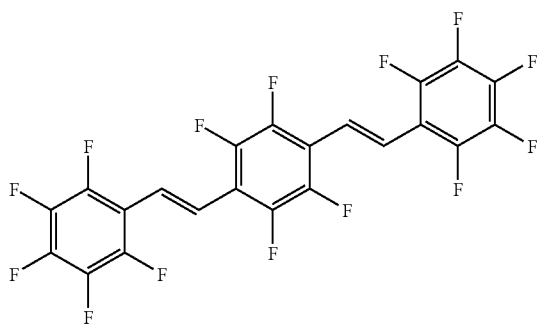
(20)
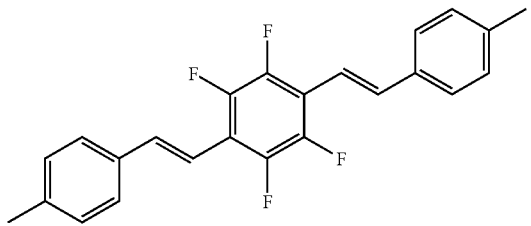
(21)
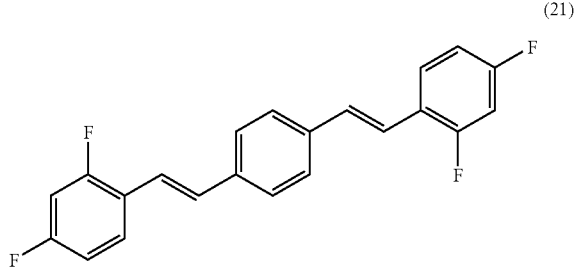

-continued
(22)
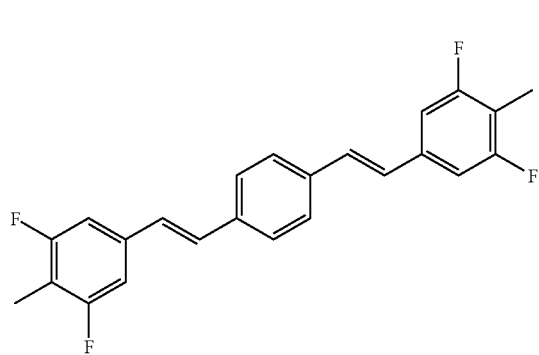
(23)
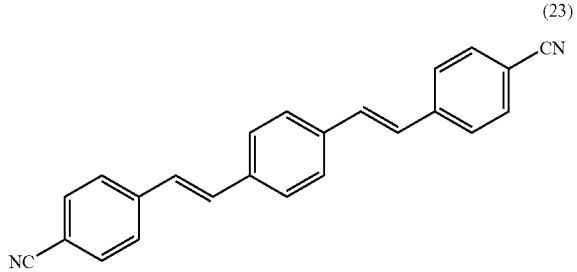
(24)
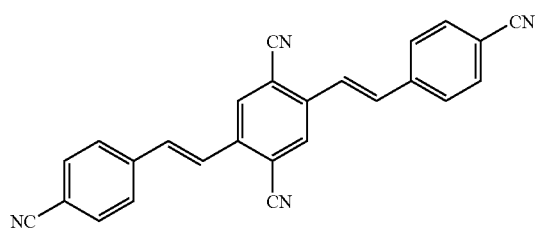
(25)
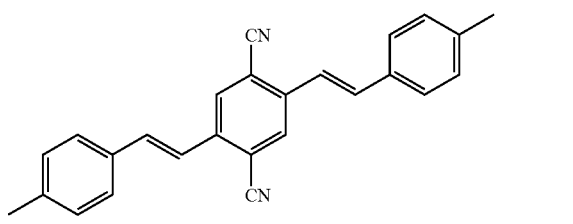
(26)
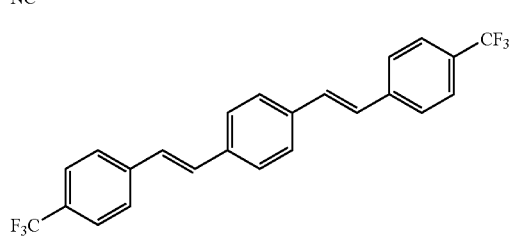
(27)
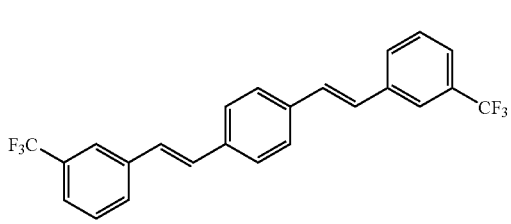
(28)
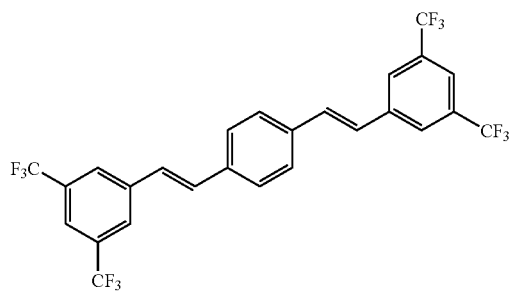
(29)
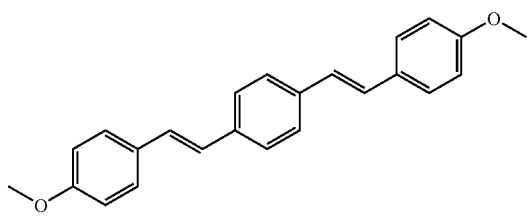
(30)
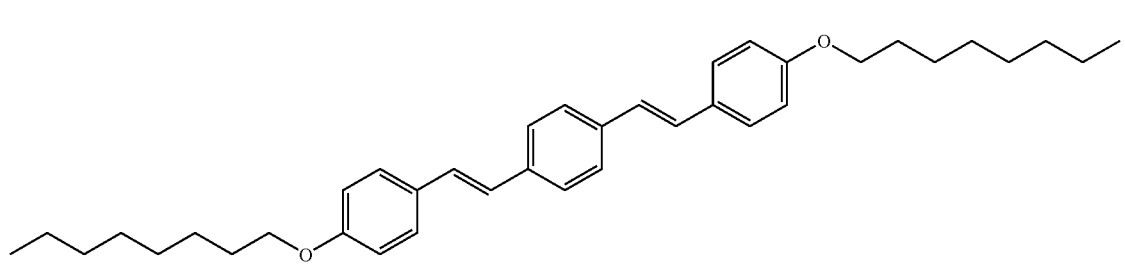
(31)
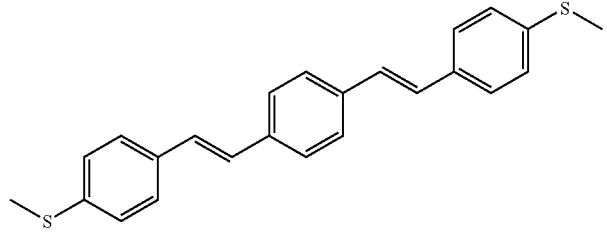

-continued
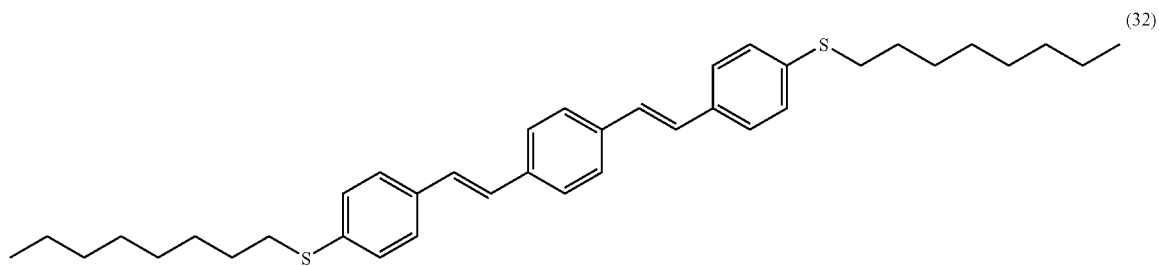
(32)
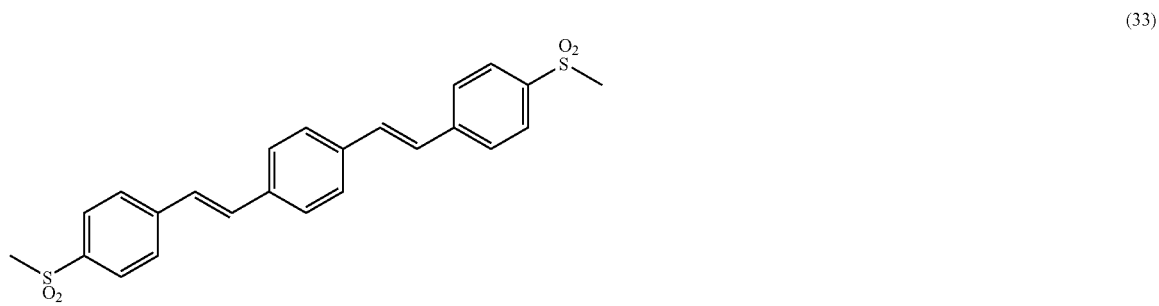
(33)
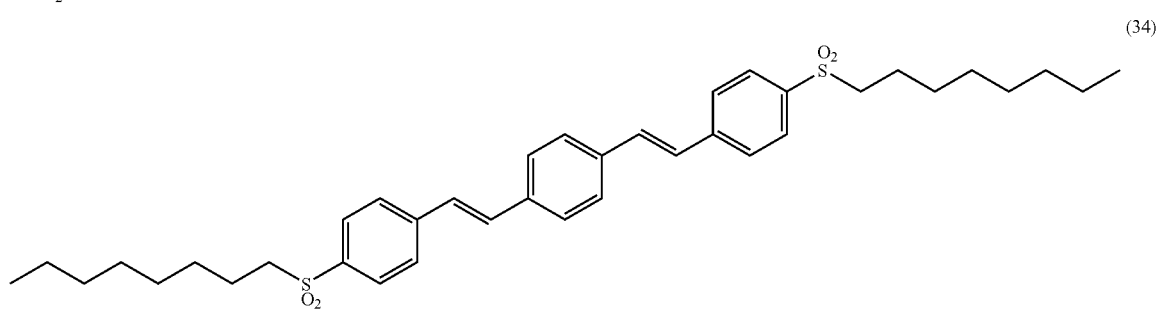
(34)
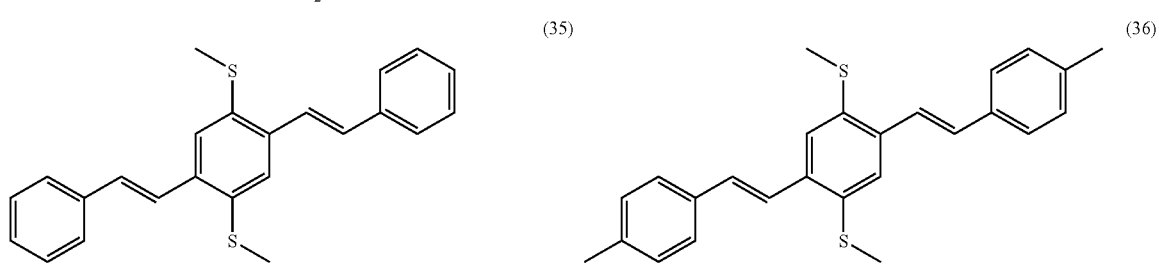
(35) (36)
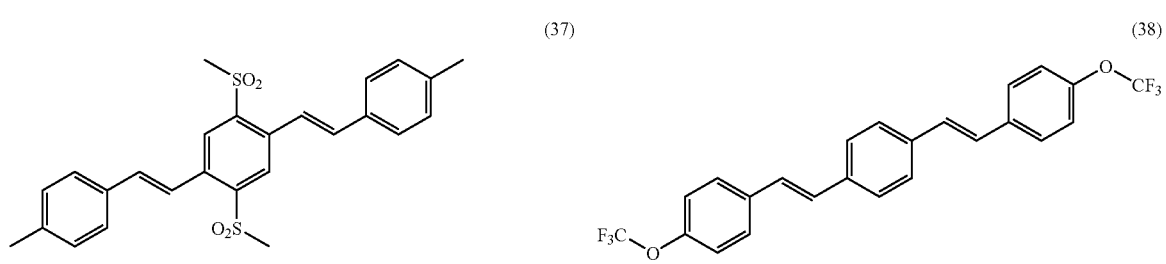
(37) (38)
(39) (40)
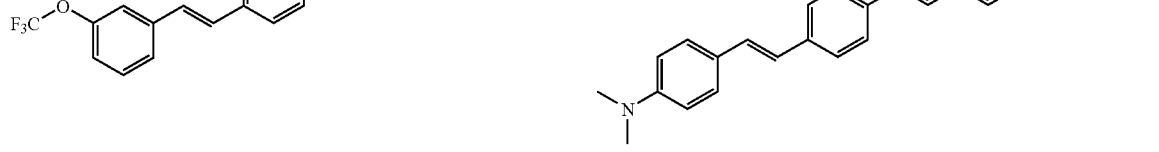

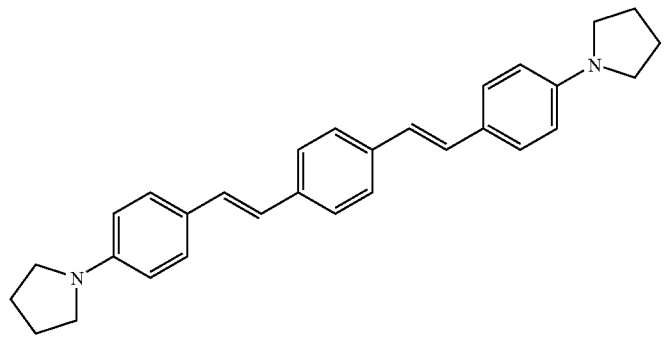
(41)
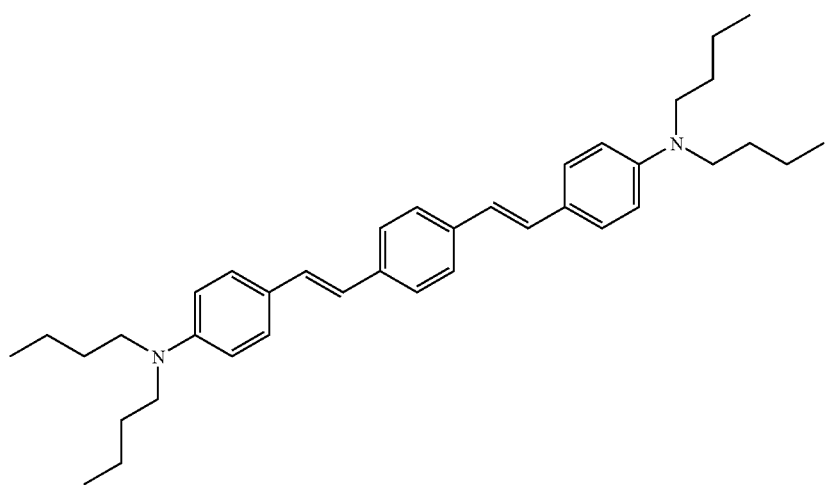
(42)
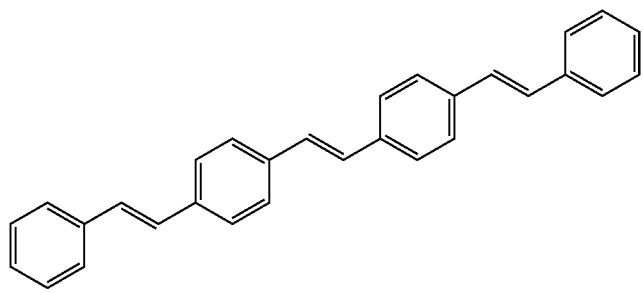
(43)
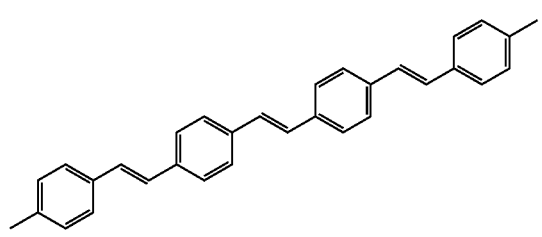
(44)
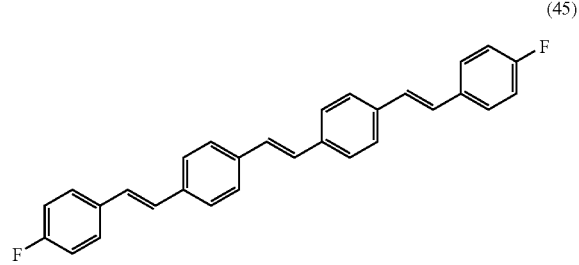
(45)

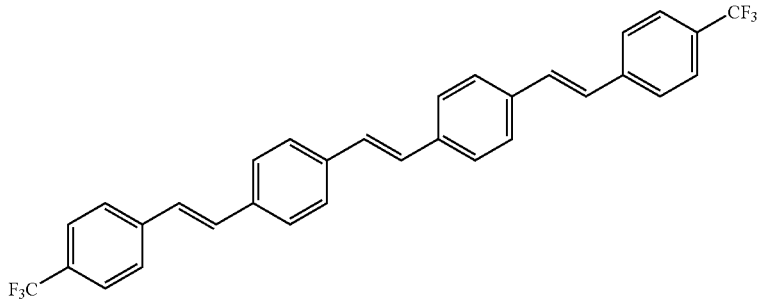
(46)
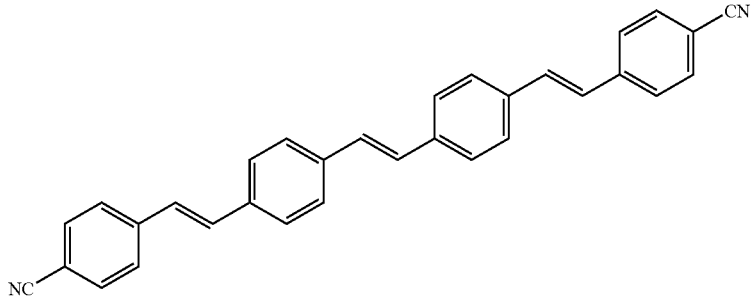
(47)
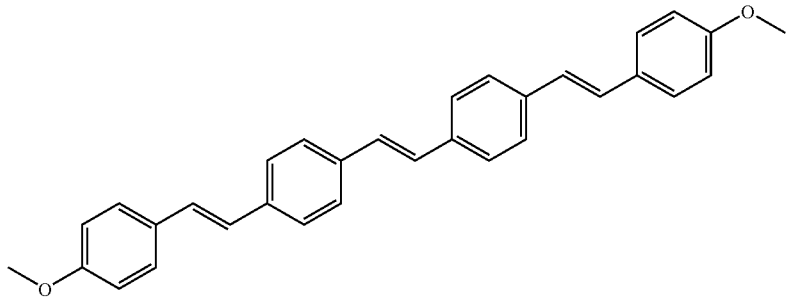
(48)
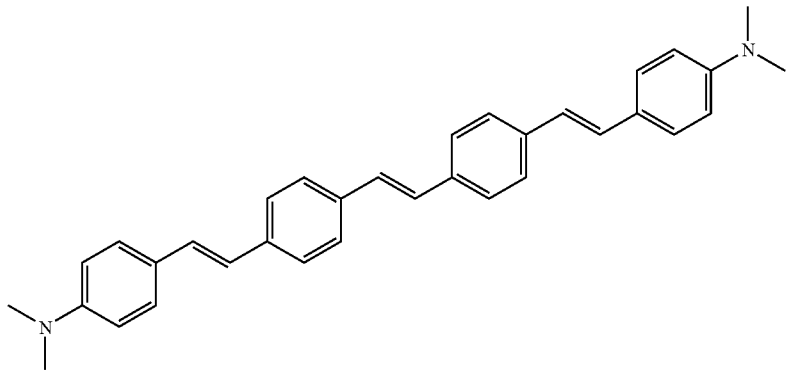
(49)
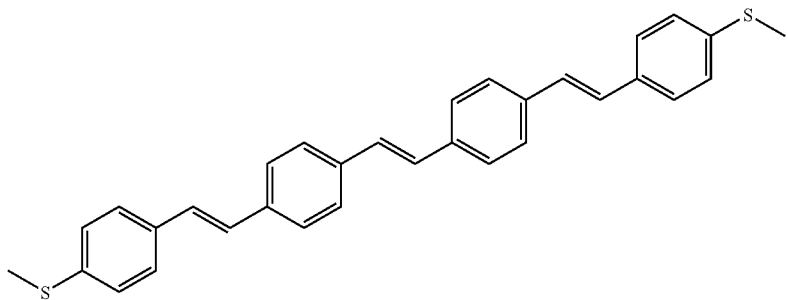
(50)

-continued
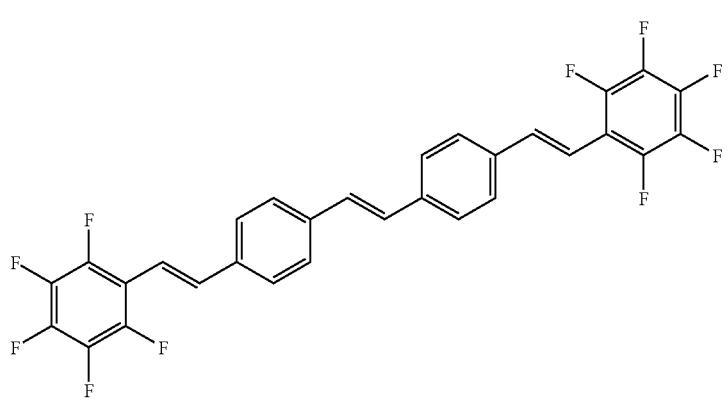
(51)
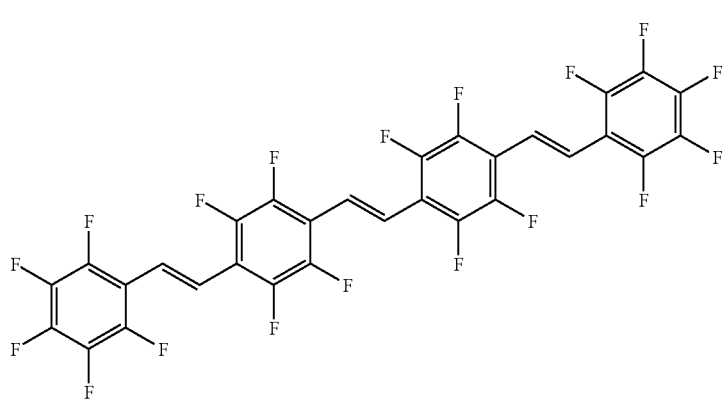
(52)
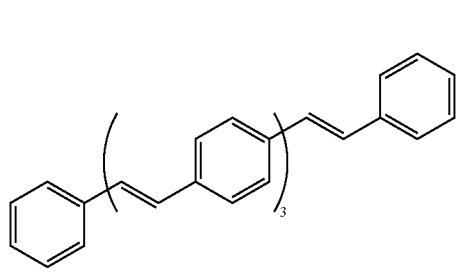
(53)
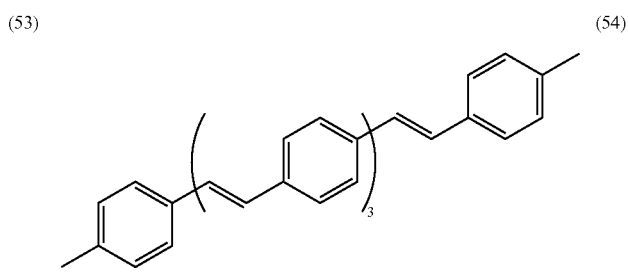
(54)
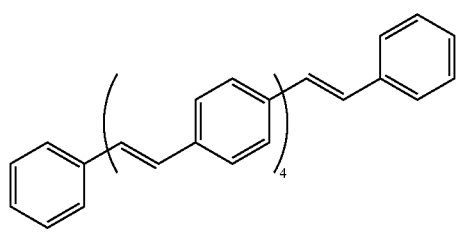
(55)
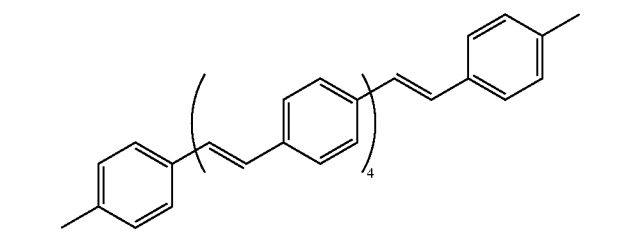
(56)
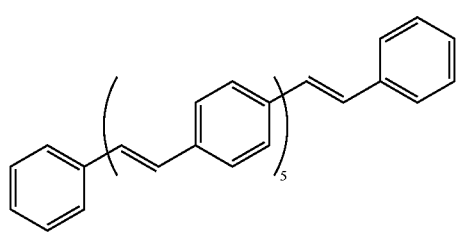
(57)
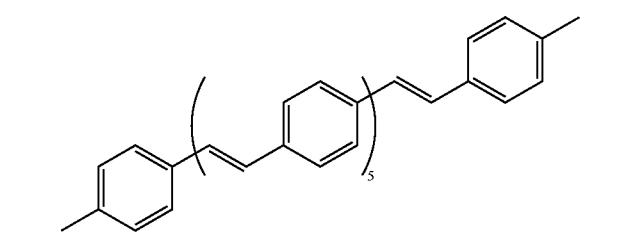
(58)

-continued
(59)
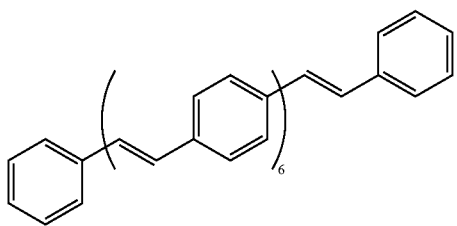
(60)
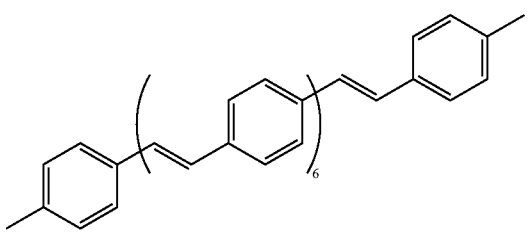
(61)
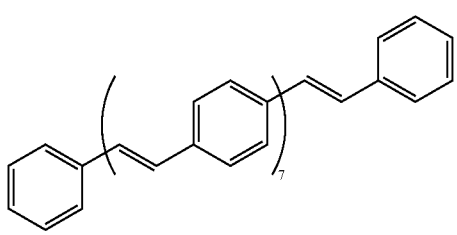
(62)
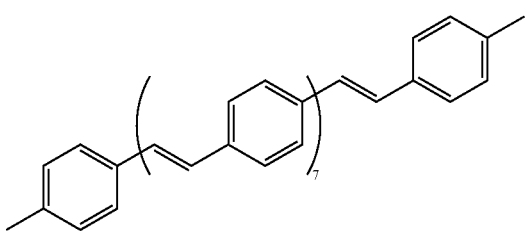
(63)
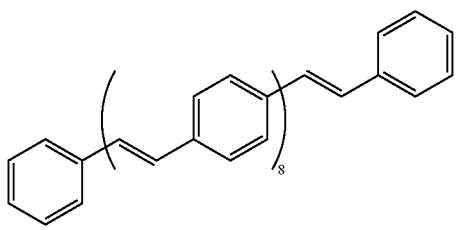
(64)
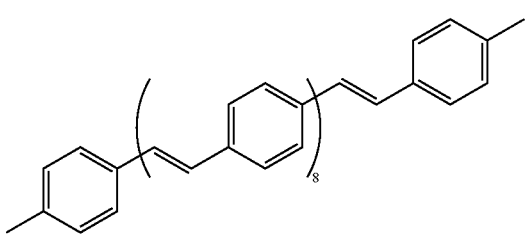
(65)
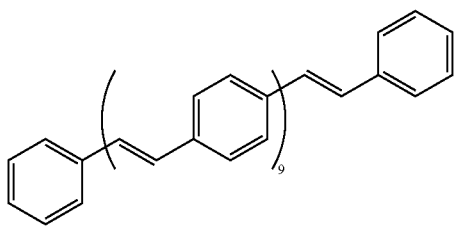
(66)
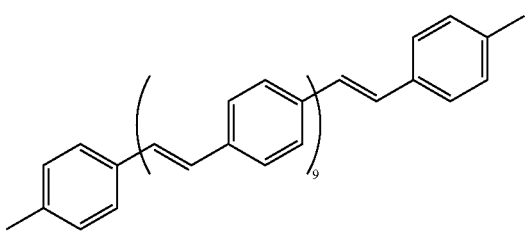
(67)
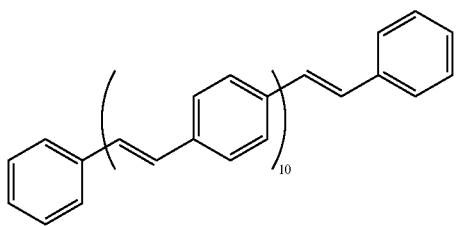
(68)
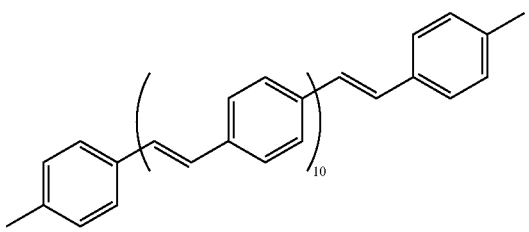
(69)
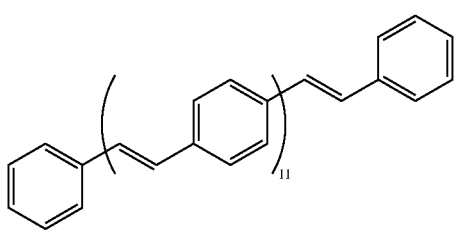
(70)
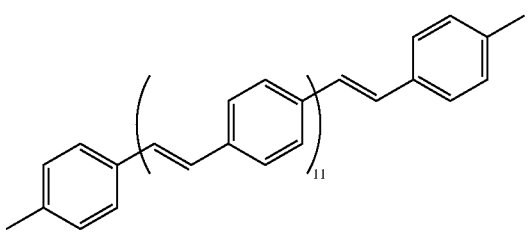

-continued
(71)
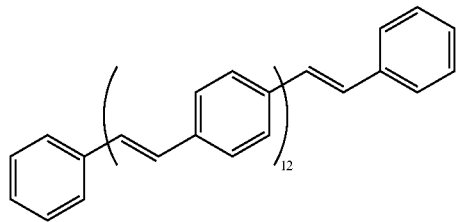
(72)
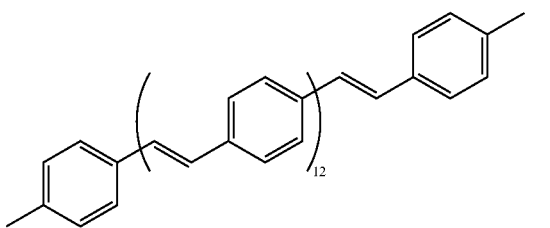
(73)
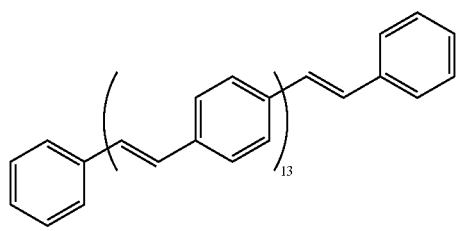
(74)
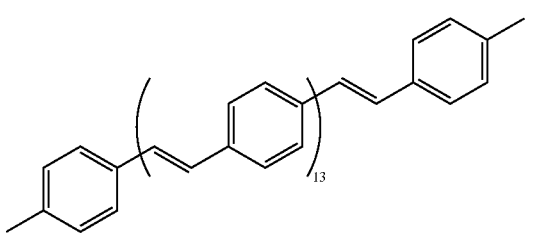
(75)
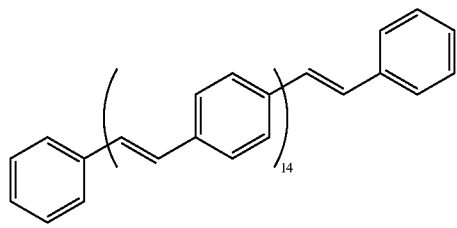
(76)
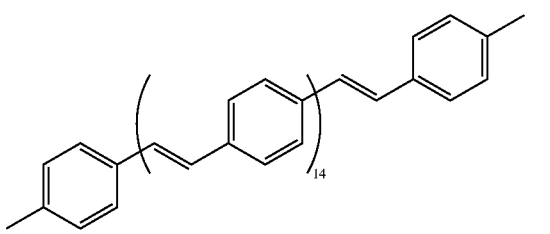
(77)
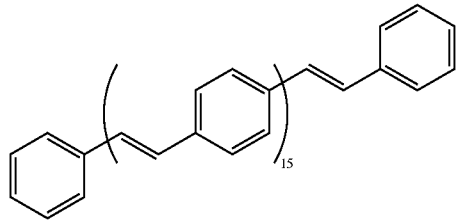
(78)
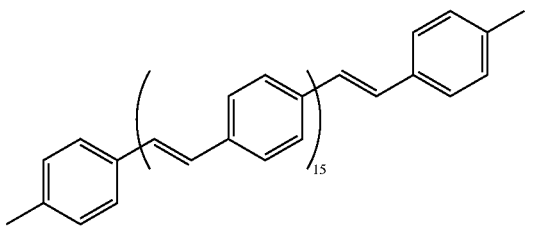
(79)
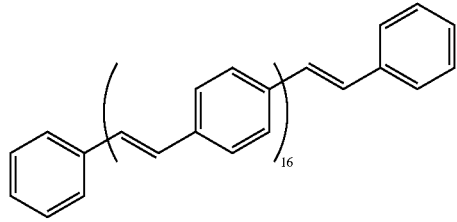
(80)
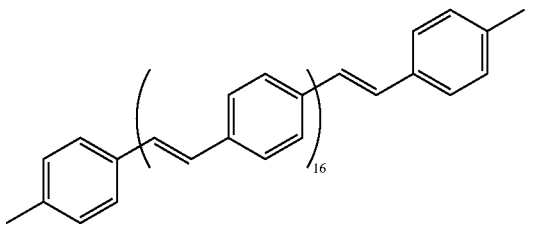
(81)
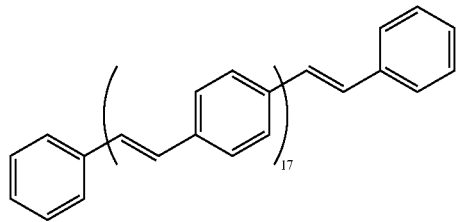
(82)
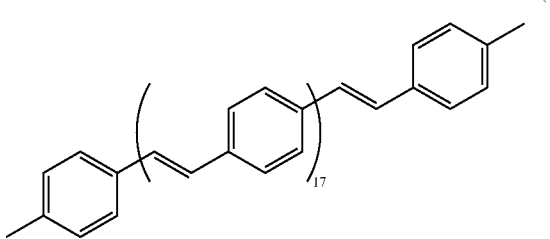

-continued
(83)
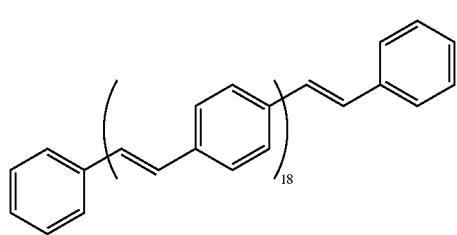
(84)
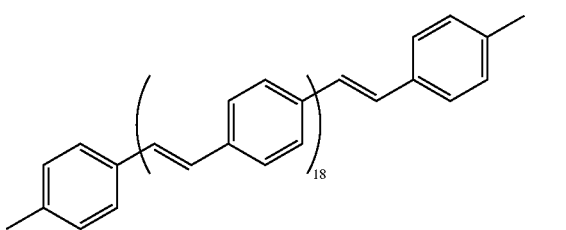
(85)
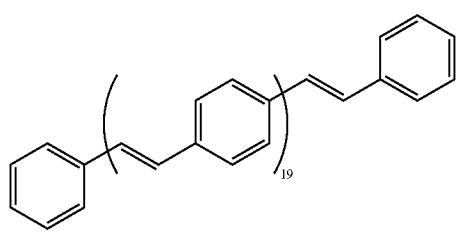
(86)
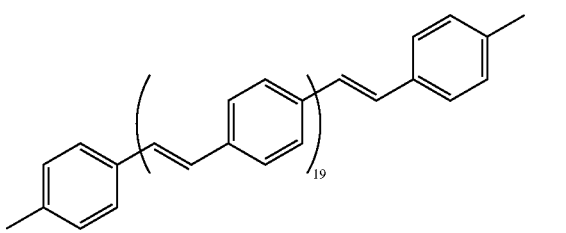
(87)
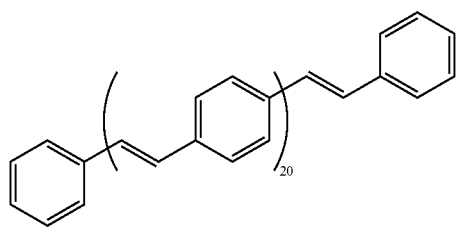
(88)
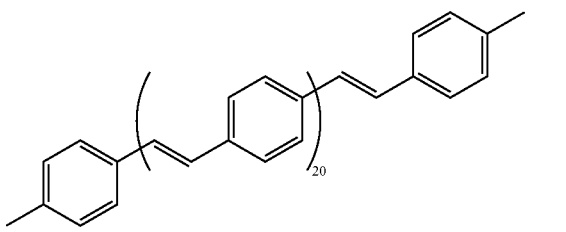
(89)
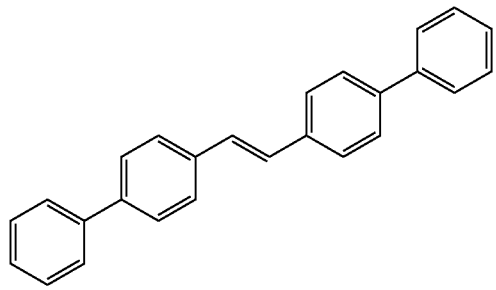
(90)
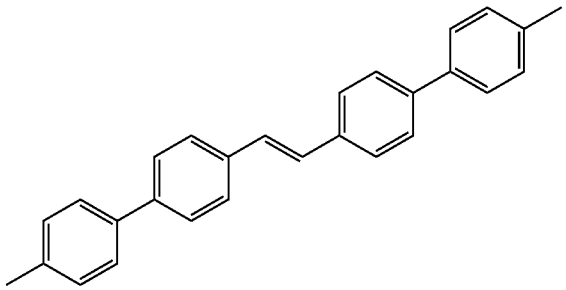
(91)
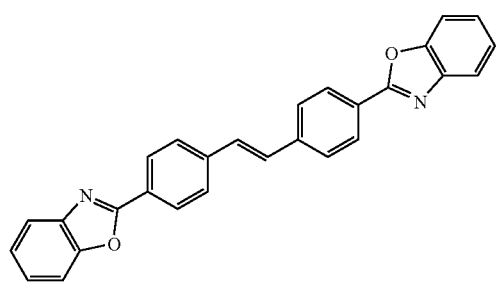
(92)
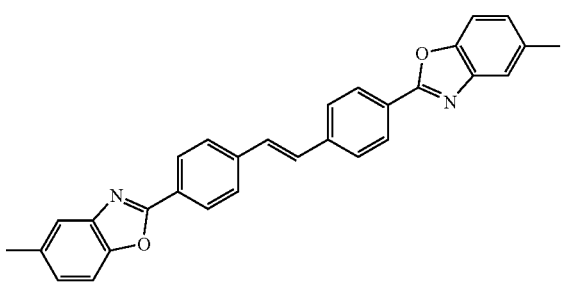

-continued
(93)
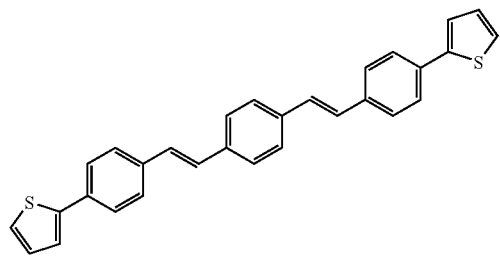
(94)
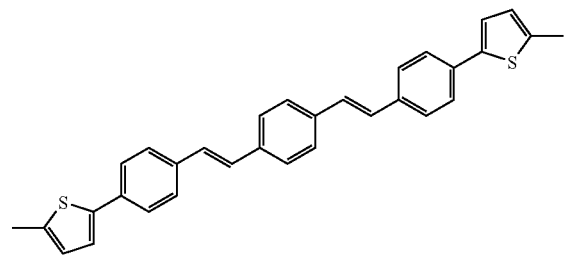
(95)
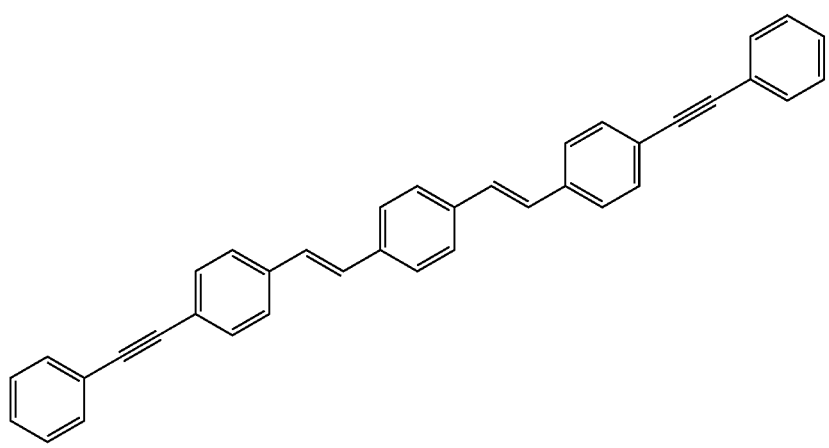
(96)
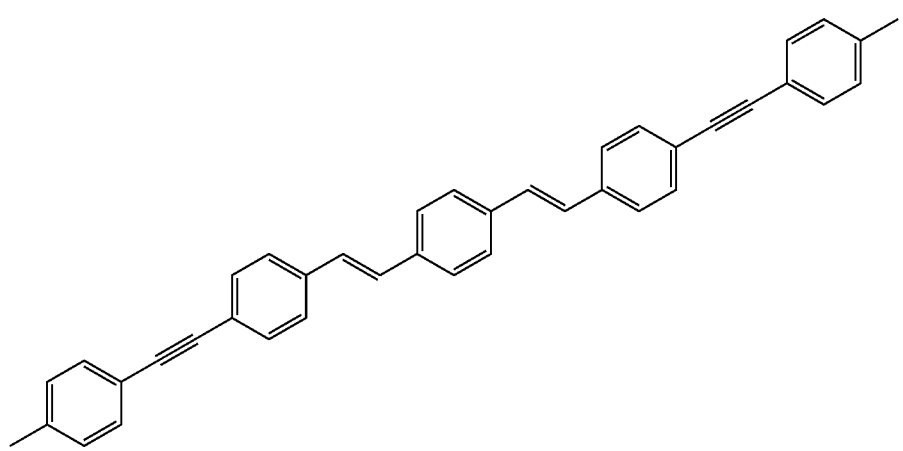
(97)
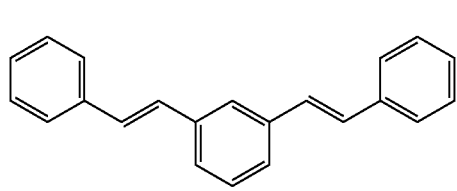
(98)
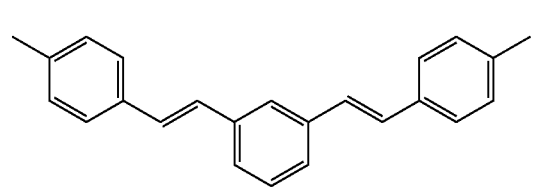
(99)
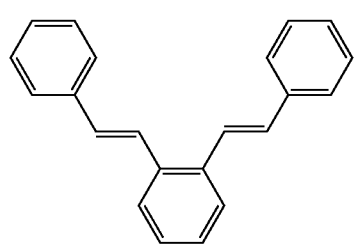
(100)
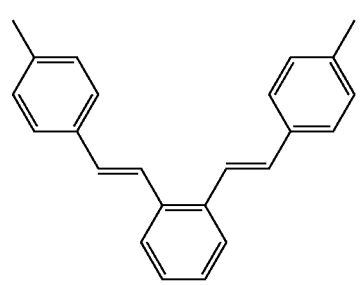

-continued

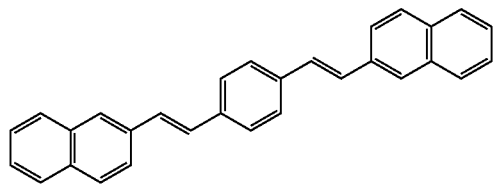
(101)

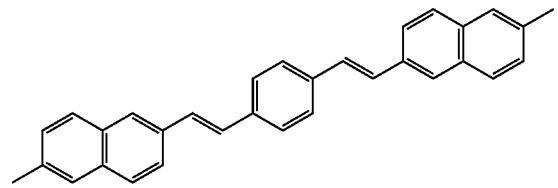
(102)

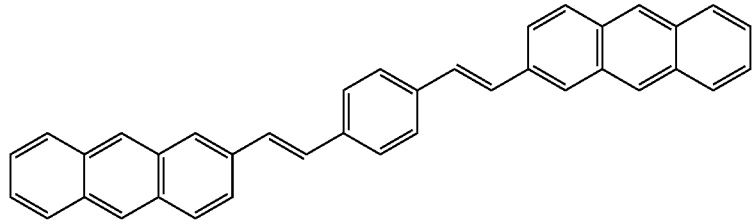
(103)

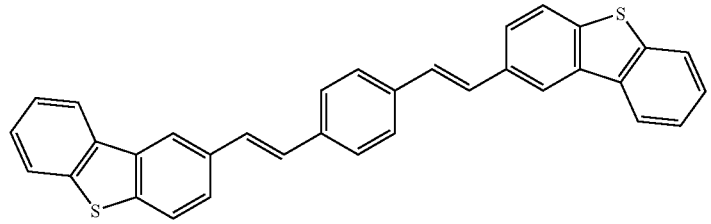
(104)

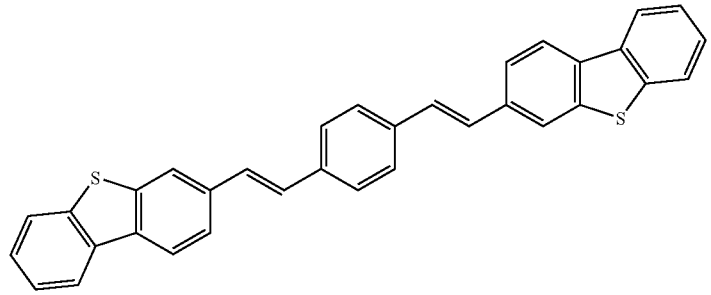
(105)

The compound employed for the organic semiconductor layer of the organic thin film transistor of the present invention can be synthesized by various kinds of synthesizing processes. Namely, it can be synthesized taking descriptions in, for example, Organic Reactions Volume 14.3 (John Wiley & Sons, Inc.), Organic Reactions Volume 25.2 (John Wiley & Sons, Inc.), Organic Reactions Volume 27.2 (John Wiley & Sons, Inc.), Organic Reactions Volume 50.1 (John Wiley & Sons, Inc.), etc., into consideration as references. Further, a steric structure at an olefin portion of the compound may be optionally arranged to a unit position isomer utilizing a thermal reaction, a photo-reaction, an addition reaction and so on.

Regarding with an electronic device such as a transistor, an employment of a material with high purity enables to get devices with high electric field-effect mobility and with high On/Off ratio. Accordingly, any optional purification procedure such as column chromatography, re-crystallization, distillation, sublimation or so is preferably conducted. A repeated conduct of the purification procedure or any combination of the above procedures preferably enables to enhance the purity. A repetition of at least twice of the sublimation purification further as the last step of the purification is desirable. In accordance with the above procedures, it is preferable to employ a material with a purity of 90% or greater measured by means of High performance liquid chromatography (HPLC). The employment of a material with high purity further preferably 95% or greater, particularly preferably 99% or greater both measured by means of HPLC enhances electric field-effect mobility and On/Off ratio of the organic thin film transistor, which enables to reveal an inherent performance of the material.

Following is a description about device structures regarding with the organic thin film transistor of the present invention.

The above device structure is not specified as far as it is a thin film transistor comprising at least three terminals consisting of a gate electrode, a source electrode and a drain electrode; an insulator layer and a novel organic semiconductor layer on a substrate, which controls its electric current flowing between the source and the drain by applying a electric voltage across the gate electrode. A device structure of public knowledge may be employable.

Among those, typical device structures of the organic thin film transistor are illustrated as Devices A, B, C and D in FIGS. 1 to 4. As the above description, a certain numbers of structures are known each about locations of the electrode, lamination sequence of layers and so on. The organic thin film transistor of the present invention has a Field Effect Transistor (FET) structure. The organic thin film transistor comprises a novel organic semiconductor layer (an organic compound layer), a source electrode and a drain electrode formed opposing each other with a predetermined space, and a gate electrode formed with predetermined distances from the source electrode and the drain electrode; and it has a structure which controls its electric current flowing between the source and the drain by applying a electric voltage across the gate electrode. In this occasion, the distance between the source electrode and the drain electrode is determined dependent on use purpose of the organic thin film transistor in the present invention, usually being 0.1 μm to 1 mm, preferably being 1 μm to 100 μm, and further preferably being 5 μm to 100 μm.

Figure 2:
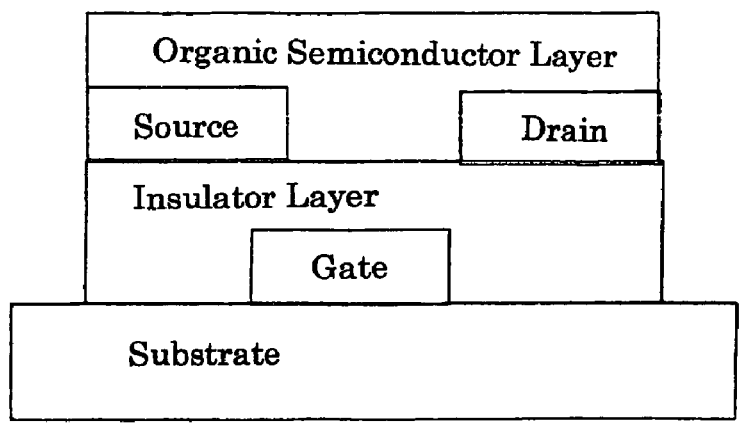
FIG. 2 is a drawing which illustrates another embodiment about device structure of an organic thin film transistor of the present invention.
Figure 3:
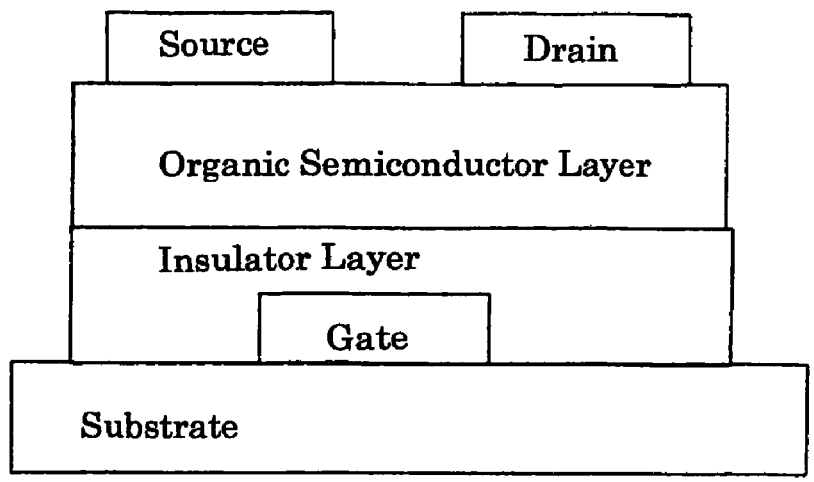
FIG. 3 is a drawing which illustrates another embodiment about device structure of an organic thin film transistor of the present invention.

Among the Devices A, B, C and D, detailed explanation about an embodiment of Device B in FIG. 2 will be described below. An organic thin film transistor having a device structure illustrated as Device B comprises a gate electrode (layer) and an insulator layer in this order on a substrate, further comprises a pair of a source electrode and a drain electrode formed with a predetermined distance each other on the insulator layer, and a novel organic semiconductor layer formed over them. The semiconductor layer forms a channel region and an electric current flowing between the source electrode and the drain electrode is controlled by a voltage applied to the gate electrode resultantly causing an On-Off operation.

Figure 5:
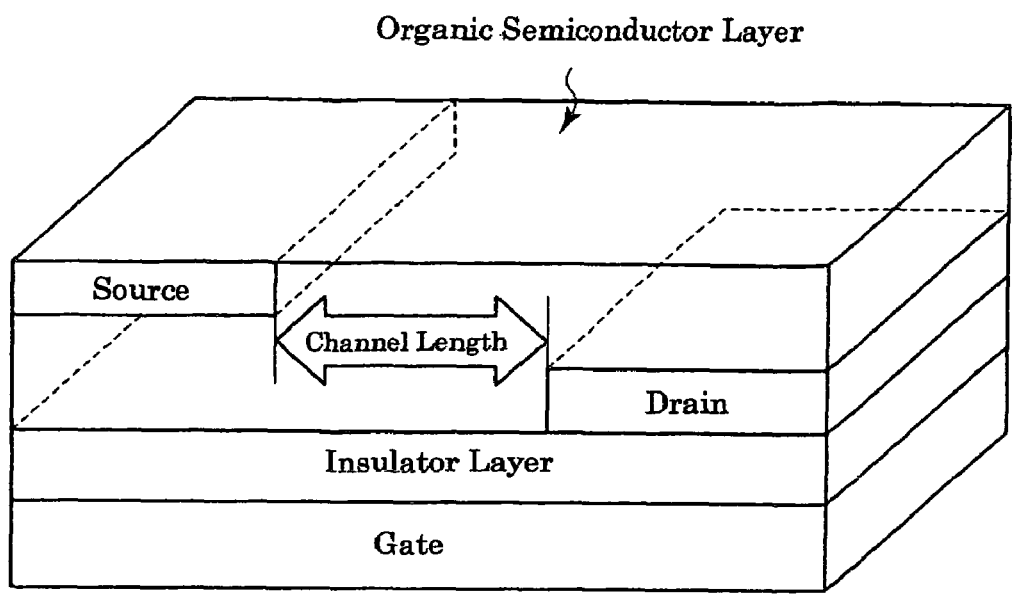
FIG. 5 is a drawing which illustrates still another embodiment about device structure of an organic thin film transistor of the present invention.
Figure 6:
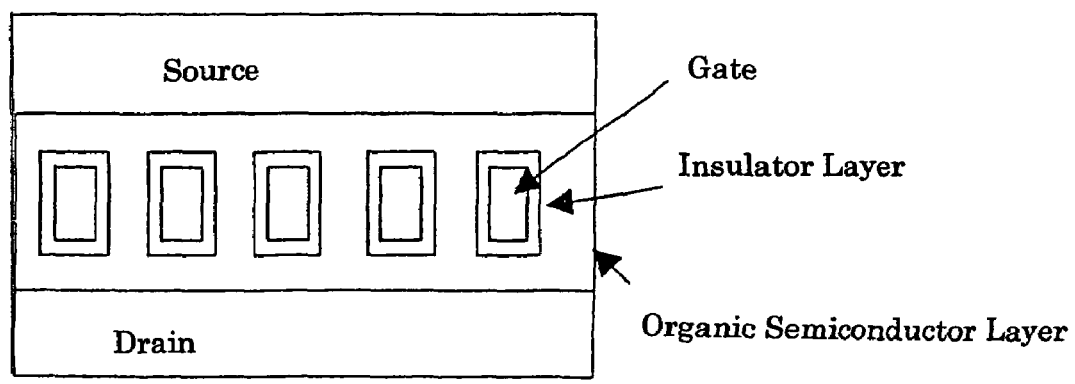
FIG. 6 is a drawing which illustrates still another embodiment about device structure of an organic thin film transistor of the present invention.

Various kinds of structures are proposed about the organic thin film transistor except the above device structures in Devices A, B, C and D of the present invention. Namely, the device structure is not specified to the above Devices A, B, C and D on the condition that it has a mechanism revealing an effect in which an electric current flowing between the source electrode and the drain electrode is controlled by a voltage applied to the gate electrode resultantly causing an On-Off operation or amplification. Examples of the device structure may include a top and bottom contact type organic thin film transistor (refer to FIG. 5) proposed in proceedings for the 49th Spring Meeting, The Japan Society of Applied Physics, 27a-M-3 (March, 2002) by Yoshida et al. in National Institute of Advanced Industrial Science and Technology, or a vertical type organic thin film transistor (refer to FIG. 6) proposed on page 1440 in IEEJ transactions 118-A (1998) by Kudo et al. of Chiba University.

(Substrate)

Figure 8:
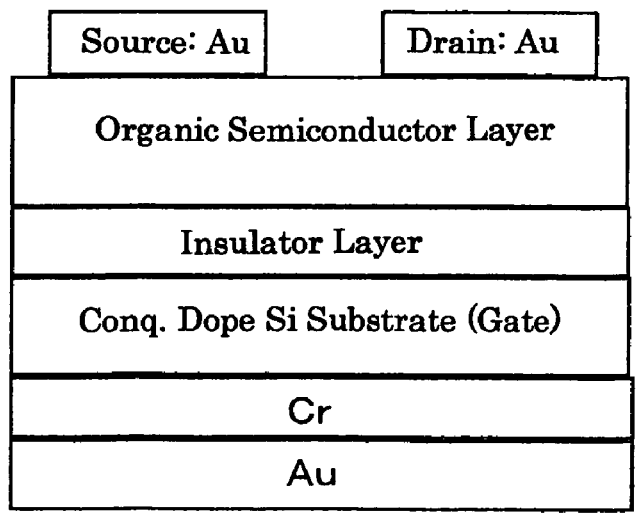
FIG. 8 is a drawing which illustrates another device structure of an organic thin film transistor in Examples of the present invention.

A substrate in the organic thin film transistor of the present invention covers a role of supporting structures for the organic thin film transistor, and aside from glasses, inorganic compound such as metal oxide or metal nitride, plastics (PET, PES and PC) or metal substrate, these composite and lamination are employable as a material for the substrate. Further, in an occasion that the structures for the thin film transistor are supported enough by means of constituting element except the substrate, the substrate may be absent. Furthermore, a silicon (Si) wafer is frequently used as a material for the substrate. In this case, Si may be used by itself as a gate electrode together with as the substrate. Still further, a surface of silicon (Si) substrate may be oxidized to form $SiO_2$, which may be utilized as an insulator layer. In this case, a metal layer employing gold (Au) and so on as an electrode for connecting a lead wire is often formed in a manner as shown in FIG. 8, on the Si substrate which is the gate electrode commonly used as the substrate.

(Electrode)

Examples of the material for the gate electrode, the source electrode and the drain electrode in the thin film transistor of the present invention are not specified as far as they are electrically conductive, and include platinum (Pt), gold (Au), silver (Ag), nickel (Ni), chromium (Cr), copper (Cu), iron (Fe), tin (Sn), antimony-lead, tantalum (Ta), indium (In), palladium (Pd), tellurium (Te), rhenium (Re), iridium (Ir), aluminum (Al), ruthenium (Ru), germanium (Ge), molybdenum (Mo), tungsten (W), tin oxide, indium oxide tin (ITO), fluorine dope zinc oxide, zinc (Zn), carbon (C), graphite, glassy carbon, silver paste and carbon paste, lithium (Li), beryllium (Be), sodium (Na), magnesium (Mg), potassium (K), calcium (Ca), scandium (Sc), titanium (Ti), manganese (Mn), zirconium (Zr), gallium (Ga), niobium (Nb), sodium-potassium alloy, magnesium/copper mixture, magnesium/silver mixture, magnesium/aluminum mixture, magnesium/indium mixture, aluminum/aluminum oxide mixture, lithium/aluminum mixture, etc.

In the organic thin film transistor of the present invention, it is preferable that the source electrode and the drain electrode are formed with a use of a fluidic material for the electrode such as a solution, a paste, an ink, a dispersed solution or so each containing the foregoing electro-conductive material. Particularly, it is preferable that the source electrode and the drain electrode is formed with a use of an electro-conductive polymer or the fluidic material for the electrode containing fine particles of a metal such as platinum, gold, silver or copper. Further, it is preferable that the solvent or the dispersive medium contains water in an amount of 60% by mass or greater, more preferably in an amount of 90% by mass or greater in order to regulate damage to the organic semiconductor. Regarding with a dispersed substance containing the fine particles of metal, for example, a publicly known electro-conductive paste may be employable, however, the dispersed substance containing the fine particles of metal having particle diameter in a range of usually from 0.5 nm to 50 nm, desirably from 1 nm to 10 nm is preferable. Examples of the metal for preparing the fine particles of metal include platinum, gold, silver, nickel, chromium, copper, iron, tin, hard lead, tantalum, indium, palladium, tellurium, rhenium, iridium, aluminum, ruthenium, germanium, molybdenum, tungsten, zinc, etc.

It is preferable that those fine particles of the metal are formed into the electrode with a use of a dispersed mixture prepared by dispersing them into a dispersant of water or an arbitrary organic solvent together with a dispersion stabilizer essentially consisting of an organic material. Examples of a process for preparing the dispersed mixture of the fine particle of metal include a physical generation process such as a vaporization process in gas, a sputtering process, a metallic vapor synthesis process or so; and a chemical generation process that generates the fine particles of the metal by reducing metal ions in liquid phase such as a colloid process, a co-precipitation process, etc. Among those, the dispersed mixtures prepared by the colloid process disclosed in Japanese Unexamined Patent Application Laid-Open Nos. Hei 11-76800, Hei 11-80647, Hei 11-319538, 2000-239853, etc; and by the vaporization process in gas disclosed in Japanese Unexamined Patent Application Laid-Open Nos. 2001-254185, 2001-53028, 2001-35255, 2000-124157, 2000-123634 and so on are preferable.

Molding the electrode with the use of the dispersed mixture of fine particles of the metal, followed by drying the solvent and then, optionally heating the molded articles in an aimed pattern at a temperature within a range of from 100° C. to 300° C., preferably within a range of from 150° C. to 200° C. will thermally adhere fused fine particles of the metal to a substrate and will form the aimed electrode pattern.

Further, it is preferable that publicly known electro-conductive polymers whose conductance is improved by doping or so are employed as the materials for the gate electrode, the source electrode and the drain electrode. Preferable examples of the electro-conductive polymer include electro-conductive polyaniline, electro-conductive polypyrrole, electro-conductive polythiophene (complex of polyethylene dihydroxy thiophene and polystyrene sulfonate), complex of polyethylene dihydroxy thiophene (PEDOT) and polystyrene sulfonate, etc. Those materials reduce the contact resistance of the thin film transistors.

Among the above examples of the material for forming the source electrode and the drain electrode, those materials having a small electric resistance at a contact surface with the organic semiconductor layer are preferable. Because the electric resistance corresponds with electric field-effect mobility in an occasion of preparing a current control device, it is necessary that the resistance is as small as possible in order for getting a large mobility. Generally, the resistance depends on a relation between a work function of the electrode material and an energy level of the organic semiconductor layer.

Assuming that the work function of the electrode material (W) is represented by a, an ionization potential (Ip) of the organic semiconductor layer is represented by b and the electron affinity (Af) of the organic semiconductor layer is represented by c; it is preferable that they satisfy a following inequality. Additionally, each of a, b and c are all positive values on bases of their vacuum levels.

In an occasion of p-type organic thin film transistor, preferably b−a<1.5 eV (Inequality (I)); more preferably b−a<1.0 eV. Although maintaining the above inequality regarding with the organic semiconductor layer enables to obtain the devices of favorable performance, it is preferable that the work function of the electrode material is selected to be as large as possible. Namely, the work function is preferably 4.0 eV or greater, more preferably 4.2 eV or greater.

The value of the work function about the metal may be selected from a list about effective metals having work function of 4.0 eV or greater described on Chemistry Manual; basic version II, page 493 (1983, third edition by the Chemical Society of Japan; published by Maruzen Co., Ltd.). The list describes that the metal having great work function is mainly Ag (4.26, 4.52, 4.64, 4.74 eV), Al (4.06, 4.24, 4.41 eV), Au (5.1, 5.37, 5.47 eV), Be (4.98 eV), Bi (4.34 eV), Cd (4.08 eV), Co (5.0 eV), Cu (4.65 eV), Fe (4.5, 4.67, 4.81 eV), Ga (4.3 eV), Hg (4.4 eV), Ir (5.42, 5.76 eV), Mn (4.1 eV), Mo (4.53, 4.55, 4.95 eV), Nb (4.02, 4.36, 4.87 eV), Ni (5.04, 5.22, 5.35 eV), Os (5.93 eV), Pb (4.25 eV), Pt (5.64 eV), Pd (5.55 eV), Re (4.72 eV), Ru (4.71 eV), Sb (4.55, 4.7 eV), Sn (4.42 eV), Ta (4.0, 4.15, 4.8 eV), Ti (4.33 eV), V (4.3 eV), W (4.47, 4.63, 5.25 eV and Zr (4.05 eV). Among those, a noble metal such as Ag, Au, Cu or Pt; and Ni, Co, Os, Fe, Ga, Ir, Mn, Mo, Pd, Re, Ru, V or W is preferable. Besides the metal, an electro-conductive polymer such as indium tin oxide (ITO), polyaniline or polyethylene dihydroxy thiophene (PEDOT) and polystyrene sulfonate (PSS); and carbon are preferable. The electrode material is not particularly specified even though it comprises one or more kinds of those substances having high work function, as far as the work function satisfies the foregoing inequality (I).

In an occasion of n-type organic thin film transistor, preferably a−c<1.5 eV (Inequality (II)), more preferably a−c<1.0 eV. Although maintaining the above inequality regarding with the organic semiconductor layer enables to obtain the devices of favorable performance, it is preferable that the work function of the electrode material is selected to be as small as possible. Namely, the work function is preferably 4.3 eV or smaller, more preferably 3.7 eV or smaller.

Specific examples of the metal having small work function may be selected from a list about effective metals having work function of 4.3 eV or smaller described on Chemistry Manual; basic version II, page 493 (1983, third edition by the Chemical Society of Japan; published by Maruzen Co., Ltd.). The list describes that the metal having small work function include Ag (4.26 eV) Al (4.06, 4.28 eV), Ba (2.52 eV), Ca (2.9 eV), Ce (2.9 eV), Cs (1.95 eV), Er (2.97 eV), Eu (2.5 eV), Gd (3.1 eV), Hf (3.9 eV), In (4.09 eV), K (2.28 eV), La (3.5 eV), Li (2.93 eV), Mg (3.66 eV), Na (2.36 eV), Nd (3.2 eV), Rb (4.25 eV), Sc (3.5 eV), Sm (2.7 eV), Ta (4.0, 4.15 eV), Y (3.1 eV), Yb (2.6 eV), Zn (3.63 eV), etc. Among those, Ba, Ca, Cs, Er, Eu, Gd, Hf, K, La, Li, Mg, Na, Nd, Rb, Y, Yb or Zn is preferable. The electrode material is not particularly specified even though it comprises one or more kinds of those substances having small work function, as far as the work function satisfies the foregoing inequality (II). However, because the metal having small work function will be easily degraded when it comes into contact with moisture or oxygen among atmospheric air, it is preferable that the metal is optionally covered by a metal such as Ag or Au which is stable among the air. Although a film-thickness necessary for covering the metal is 10 nm or more, and although a thicker film-thickness enables to protect the metals from contacting with oxygen or water, it is preferable that the film-thickness is determined up to 1 μm by reasons of practice and productivity.

Regarding with a process for forming the electrode, they may be formed in accordance with, for example, a vapor deposition process, an electron beam vapor deposition process, a sputtering process, an atmospheric pressure plasma process, an ion plating process, a chemical vapor phase vapor deposition process, an electro-deposition process, an electroless plating process, a spin coating process, a printing process or an of ink-jet process, etc. Further, regarding with a patterning process which may be optionally carried out to the above resultant electro-conductive film, there is an electrode formation process with a use of a well-known photolithographic process or lift-off process, and an etching process after forming a photoresist over a metal foil such as aluminum or copper by means of heat transfer, ink-jet, etc. Furthermore, the patterning process may be carried out directly by ink-jetting a solution or a dispersed solution of the electro-conductive polymer, or a dispersed solution containing the fine particles of the metal; or may be carried out with a use of a lithograph or a laser abrasion against a coated film. Moreover, the patterning may be also carried out using a printing process such as a relief printing, an intaglio printing, a planographic printing, a screen printing and so on employing an electro-conductive ink comprising the electro-conductive polymer or the fine particles of metal or an electro-conductive paste.

The film-thickness of the resultant electrode is not particularly specified as far as the electrode is electrically conductive, however, the film-thickness falls within a range of preferably from 0.2 nm to 10 μm, more preferably from 4 nm to 300 nm. When it falls within the preferable range, any voltage drop will be prevented because a high electric resistance dependent on a thin film-thickness never exists. Moreover, the film-thickness without exceeding the above range does not require long time for the film-formation, and further, even when other layers such as a protective layer and an organic semiconductor layer are laminated on the electrode, the laminated layers will be smooth without suffering from a generation of bumps.

Furthermore in the organic thin film transistor of the invention, for example, a buffer layer may be sandwiched between the organic semiconductor layer and a pair of the source electrode and the drain electrode in order to improve carrier injection efficiency. Alkali metals such as LiF, $Li_2O$, CsF, $NaCO_3$, KCl, $MgF_2$, $CaCO_3$ and so on used for a cathode of an organic electroluminescence device, or a compound having alkaline earth metal ionic bond are preferable as the buffer layer for the n-type organic thin film transistor.

(Insulator Layer)

Materials for the insulator layer in the organic thin film transistor of the present invention are not specified as far as they are electrically insulative and having ability of being formed into a thin film. Materials such as a metal oxide (including oxide of silicon), a metal nitride (including nitride of silicon), a polymer, and an organic low molecular compound each having an electric resistivity of 10 Ωcm or greater at a room temperature may be employable and an inorganic oxide film having high dielectric constant is preferable as the material for the insulator layer.

Examples of the inorganic oxide include silicon oxide, aluminum oxide, tantalum oxide, titanium oxide, tin oxide, vanadium oxide, barium titanate strontium, zirconic acid barium titanate, zirconic acid lead titanate, lead titanate lanthanum, strontium titanate, barium titanate, barium fluoride magnesium, lanthanum oxide, fluorine oxide, magnesium oxide, bismuth oxide, titanic acid bismuth, niobium oxide, strontium titanate bismuth, tantalic acid strontium bismuth, tantalum pentoxide, tantalic acid niobic acid bismuth, trioxide yttrium, and any combination of those. Among those, silicon oxide, aluminum oxide, tantalum oxide and titanium oxide are preferable. Further, inorganic nitride-based compound such as silicon nitride ($Si_3N_4$, $Si_xN_y$ (x, y>0)), aluminum nitride and so on are preferable as the material for the insulator layer.

Further, the insulator layer may be formed with a precursor including alkoxide metal. For example, applying a solution prepared by dissolving the precursor over the substrate, followed by chemical solution treatment or heat treatment will form the insulator layer.

The metal in the above alkoxide metal is selected from transition metal, lanthanoid or main group element, and specific examples include barium (Ba), strontium (Sr), titanium (Ti), bismuth (Bi), tantalum (Ta), zircon (Zr), iron (Fe), nickel (Ni), manganese (Mn), lead (Pb), lanthanum (La), lithium (Li), sodium (Na), potassium (K), rubidium (Rb), cesium (Cs), francium (Fr) berylium (Be) magnesium (Mg), calcium (Ca), niobium (Nb), thallium (Tl), mercury (Hg), copper (Cu), cobalt (Co), rhodium (Rh), scandium (Sc), yttrium (Y), etc. Further, examples of the alkoxide in the above alkoxide metal are derived from alcohols including methanol, ethanol, propanol, isopropanol, butanol, isobutanol, etc.; or alkoxy alcohols including methoxyethanol, ethoxyethanol, propoxyethanol, butoxyethanol, pentoxyethanol, heptoxyethanol, methoxypropanol, ethoxypropanol, propoxypropanol, butoxypropanol, pentoxypropanol, heptoxypropanol, etc.

In the present invention, employing the above material for the insulator layer easily generates a depletion layer among the insulator layer and as a result, enables to reduce a threshold voltage of transistor operation. Particularly, employing silicon nitrides such as $Si_3N_4$, $Si_xN_y$, $SiON_x$ (x, y>0) and so on among the above materials for the insulator layer more easily generates a depletion layer among the insulator layer and as a result, enables to further reduce a threshold voltage of transistor operation. Regarding with the insulator layer employing an organic compound, polyimide, polyamide, polyester, polyacrylates, photo-curable resin of photo-radical polymerization-based or photo cation polymerization-based, copolymer containing an acrylonitrile component, polyvinyl phenol, polyvinyl alcohol, novolac resin, cyanoethylpullulan, and so on are employable as the materials.

Additionally, wax, polyethylene, polychloropyrene, polyethyleneterephthalate, polyoxymethylene, polyvinylchloride, polyvinylidenefluoride, polymethylmethacrylate, polysulfon, polycarbonate, polyimidecyanoethylpullulan, poly(vinylphenol) (PVP), poly(methylmethacrylate) (PMMA), polycarbonate (PC), polystyrene (PS), polyolefin, polyacrylamide, poly(acrylic acid), novolac resin, resol resin, polyimide, polyxylylene, epoxide resin and further, high molecular materials having high dielectric constant such as pullulan are employable as the materials for the insulator layer.

Particularly preferable material for the insulator layer is an organic compound having repellency. The repellency suppresses an interaction between the insulator layer and the organic semiconductor layer and raises crystallinity of the organic semiconductor layer taking advantage of the cohesiveness inherent in the organic semiconductor, which improves the device performance. Examples include polyparaxylylene derivative disclosed in Yasuda et al., Jpn. J. Appl. Phys. Vol. 42 (2003) pp. 6614-6618; and the organic compound disclosed in Janos Veres et al., Chem. Mater., Vol. 16 (2004) pp. 4543-4555.

Figure 4:
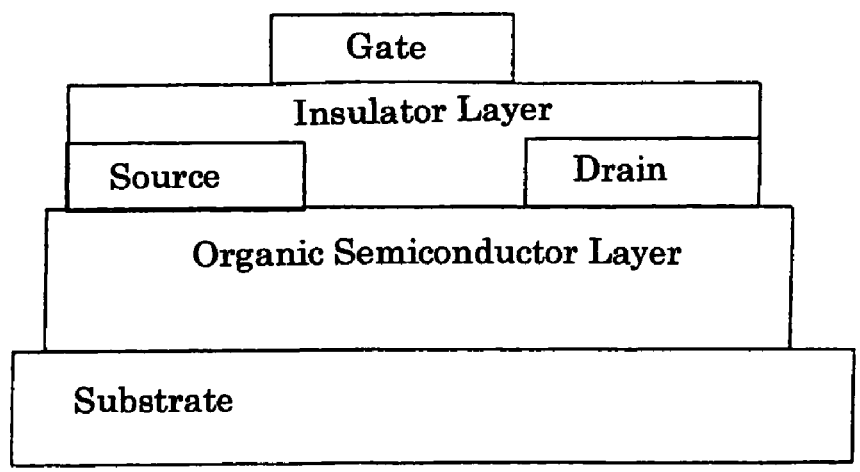
FIG. 4 is a drawing which illustrates another embodiment about device structure of an organic thin film transistor of the present invention.

Further, when top gate structures illustrated in FIGS. 1 and 4 are used, employing the above organic compound as the material for the insulator layer is an effective skill for forming a film with little damage against the organic semiconductor layer.

The above insulator layer may be a mixed layer employing plural of the inorganic or organic compounds, or may be a laminated structure of multilayer. In this occasion, the device performance is controllable by optionally mixing both the material having high dielectric constant and the material having repellency, or by laminating multilayer.

Further, the insulator layer may be an anodic oxide film, or may contain the anodic oxide film as its constituent. It is preferable that a sealing of anodic oxide coating is further applied to the anodic oxide film. The anodic oxide film is formed by anodically oxidizing an anodic oxidizable metal in accordance with a well known process. Aluminum or tantalum may be exemplified as the anodic oxidizable metal; and the process for anodic oxidation is not particularly specified permitting a publicly known process. The anodic oxidation treatment forms the oxide film. Any electrolytic solution capable of forming a porous oxide film may be employable as an electrolytic solution for the anodic oxidation treatment. Generally, sulfuric acid, orthophosphoric acid, oxalate, chromic acid, boric acid, sulfamic acid, benzenesulfonic acid and so on; or a mixed acid made by combining 2 or more kinds of those acids or those salt are employable as the electrolytic solution for the anodic oxidation treatment.

Although a condition for the electrolytic solution for the anodic oxidation treatment variously changes depending on the electrolytic solution, it is generally appropriate that the concentration of the electrolytic solution is within a range from 1 to 80% by mass, the temperature of the electrolytic solution is within a range of from 5 to 70° C., the current density is within a range of from 0.5 to 60 A/cm$^2$, the voltage within a range of from 1 to 100 volt, and that the time of electrolytic treatment is within a range of from 10 seconds to 5 minutes. A preferable anodic oxidation treatment is a process employing an aqueous solution of sulfuric acid, phosphoric acid or boric acid as electrolytic solution; and treating with direct current, however, alternating current may be applicable. In this occasion, the concentration of those acids is preferably within a range of from 5 to 45% by mass, the temperature of the electrolytic solution is preferably within a range of from 20 to 50° C., the current density is preferably within a range of from 0.5 to 20 A/cm² and the time of electrolytic treatment is preferably within a range of from 20 to 250 seconds.

Regarding with a thickness of the insulator layer, a thin thickness will enhance an effectiveness voltage applied across the organic semiconductor. Accordingly, it is possible to reduce both a driving voltage and a threshold voltage of the device itself, however on the contrary, because a leak current between the source electrode and the gate electrode will increase, it is necessary to select an appropriate film thickness. The film thickness is preferably within a range from 10 nm to 5 µm, more preferably within a range from 100 nm to 1 µm.

Further, an arbitrary orientation treatment may be carried out to a region between the insulator layer and the organic semiconductor layer. A preferable example of the orientation treatment is a method conducting a water repelling treatment to a surface of the insulator layer thereby reducing a mutual action between the insulator layer and the organic semiconductor layer and as a result, improving crystallinity of the organic semiconductor layer. Specific example is a method that forms a self-assembling monolayer (SAM) by bringing materials for making the self-assembling orientation film like silane coupling agent such as octadecyl trichlorosilane, trichloromethyl silazane, alkane orthophosphoric acid, alkane sulfonic acid, alkane carboxylic acid or so into contact with the surface of the insulator layer in the state of a liquid phase or a gas phase, followed by appropriately drying. Furthermore, exactly as practically used in the orientation of the liquid crystal device, a method of disposing a film consisting of polyimide or so over the surface of the insulator layer followed by conducting a rubbing treatment to the surface is also preferable.

Examples of the process for forming the above insulator layer include vacuum vapor deposition process, molecular beam epitaxial growth process, ion cluster beam process, low energy ion beam process, ion plating process, chemical vapor deposition (CVD) process, sputtering process; dry processes such as atmospheric pressure plasma process described in Japanese Unexamined Patent Application Laid-Open Nos. Hei 11-61406, Hei 11-133205, 2000-121804, 2000-147209 and 2000-185362; a wet process like a coating process such as a spray coating process, a spin coating process, a blade coating process, a dip coating process, a casting process, a roller coating process, a bar coating process, a die coating process or so; and like patterning processes such as printing or ink-jet, etc. They are applicable depending on the materials. The wet processes include a process of coating and drying a solution prepared by dispersing fine particles of inorganic oxide into an arbitrary organic solvent or water with an optional use of an assistant dispersion agent like surfactants; or a so-called sol-gel process of coating and drying an oxide precursor, for example, solution of alkoxide article.

Although the film thickness of the organic semiconductor layer in the organic thin film transistor of the present invention is not particularly specified, it is usually within a range of from several nm to 1 µm, and preferably within a range of from 10 nm to 250 nm.

Further, although a process for forming the organic semiconductor layer is not particularly specified, various kinds of well-known processes such as a molecular beam evaporation process (MBE process); a vacuum vapor deposition process; a chemical vapor deposition process; a printing or coating process of a solution prepared by dissolving a material into a solvent, such as a dipping process, a spin coating process, a casting process, a bar coating process, a roller coating process, etc.; a baking process; electro-polymerization process; a molecular beam adhesion process; a self-assembly process from solution; are employable singly or in combination with the use of the above materials for the organic semiconductor layer.

Because improving the crystallinity of the organic semiconductor layer will improve the field-effect mobility, it is desirable to maintain the temperature of the substrate in the film-formation at high temperature when a film-formation from the air phase (vapor deposition, sputtering, etc) is used. The temperature is preferably within a range of from 50 to 250° C., more preferably within a range of from 70 to 150° C. Further, carrying out an annealing after the film-formation without concerning about a process for film-formation is preferable because devices of high performance are obtained. The annealing temperature is preferably within a range of from 50 to 200° C., more preferably within a range of from 70 to 200° C. The annealing time is preferably within a range of from 10 minutes to 12 hours, more preferably within a range of from 1 to 10 hours.

In the present invention, one kind of material selected from a group consisting of the styryl derivative, distyryl derivative and a styryl compound represented by the general formula (a) may be employed for the organic semiconductor layer. Any combination of 2 or more kinds of the materials among the above group, and plural mixed thin film or multilayer each employing public known semiconductor such as pentacene or thiophene may be also employed for the organic semiconductor layer.

Although a method for forming the organic thin film transistor of the present invention may be in accordance with any well-known method without particularly specified, a serial successive steps for preparing the device comprising placing a substrate, forming a gate electrode, forming an insulator layer, forming an organic semiconductor layer, forming a source electrode and forming a drain electrode all without contacting with an atmosphere perfectly is preferable because it enables to prevent disturbance against the device performance caused by moisture or oxygen among the atmosphere in contact. In an occasion that any one of the above steps being unable to evade contacting with the atmosphere, it is desirable that a step of forming an organic semiconductor layer and all following steps never contact with the atmosphere and that the organic semiconductor layer should be laminated after cleaning and activating a surface over which the organic semiconductor layer is to be laminated, e.g., a surface over which a source electrode and a drain electrode were partially laminated in the case of the foregoing Device B, by means of ultraviolet irradiation, ultraviolet/ozone irradiation, oxygen plasma, argon plasma, etc., just before forming the organic semiconductor layer.

Further for example, considering about an influence of oxygen and water contained in atmospheric air upon the organic semiconductor layer, a gas barrier layer may be formed over entire or partial surface of outer face of the organic transistor device. Regarding with a material for forming the gas barrier layer, any substance usually employed in this technical field may be employable. Examples include polyvinyl alcohol, ethylene-vinyl alcohol copolymer, polyvinylchloride, polyvinylidene chloride, polychlorotrifloroethylene, etc. Furthermore, the inorganic substances having an insulating capability exemplified about the insulator layer are also employable.

EXAMPLES

The present invention will be described more specifically with reference to Examples and Synthesis Examples in the following.

Synthesis Example 1 (Synthesis of Compound (1))

Under an atmospheric nitrogen gas and at a room temperature, adding a methanol solution of sodium methoxide (28%, 0.43 g) into a methanol solution (5 milliliter) of benziltriphenylphosphoniumchloride (0.87 g) and after stirring the resultant solution for 1 hour, terephthal aldehyde (0.13 g) was added slowly to the reacted mixture solution and the solution was stirred overnight. Adding water to the reacted mixture solution, precipitated crystals were separated by filtration and washed with the use of water and methanol. Dissolving the resultant crystal into decalin with a temperature of 160° C. and adding iodine, the resultant solution was stirred for 2 hours. Then, a crystal generated after cooling with ice was separated by filtration, washed with the use of decalin and hexane, re-crystallized by toluene, purified by sublimation and as a result, the foregoing Compound (1) (0.18 g) was obtained.

Example 1

An organic thin film transistor was prepared in accordance with following steps. At first, after ultrasonically cleaning a glass substrate with the use of neutral detergent, pure water, acetone and ethanol spending each 30 minutes respectively, a film of gold (Au) having a thickness of 40 nm was formed on the substrate in accordance with a sputtering process resultantly making a gate electrode. Subsequently, the substrate was set on a film-forming zone of a thermal CVD equipment. On the other hand, polyparaxylene derivative [polyparaxylene chloride (parylene)] (trade name: diX-C; available from Daisan KASEI CO., LTD.) as a material for an insulator layer in an amount of 250 mg was placed in a Petri dish and installed into an evaporation zone of the material. Vacuuming the thermal CVD equipment by means of a vacuum pump and after depressurizing it down to a pressure of 5 Pa, both the evaporation zone and a polymerization zone were heated up to the temperature of 180° C. and 680° C. respectively. By leaving the material in the same situation for 2 hours, an insulator layer with a thickness of 1 μm was formed over the gate electrode.

Figure 7:
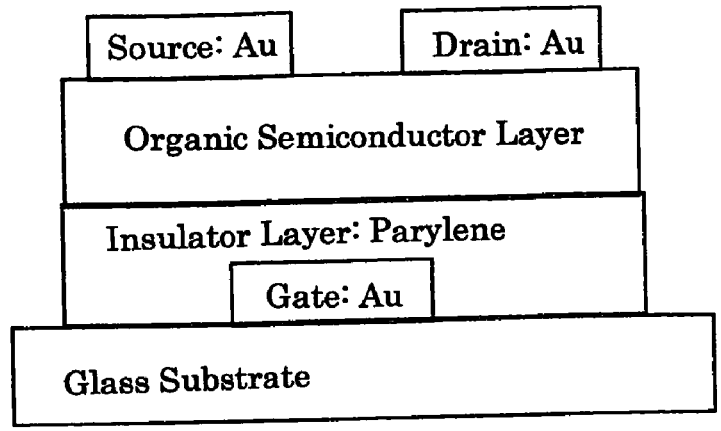
FIG. 7 is a drawing which illustrates a device structure of an organic thin film transistor in Examples of the present invention.

Then, the substrate was set in a vacuum vapor deposition apparatus (EX-400; manufactured by ULVAC Co.) and the above Compound (1) was formed into a film of an organic semiconductor layer with a thickness of 50 nm at a vapor deposition rate of 0.05 nm/second over the insulator layer. Subsequently, a source electrode and a drain electrode separated with a distance (channel length: L) of 75 μm between each other without contacting each other were provided by forming a gold film having a thickness of 50 nm through metal masking. Widths (channel widths Ws) of both the source electrode and the drain electrode were formed so as to be 5 mm respectively. (refer to FIG. 7)

Figure 9:
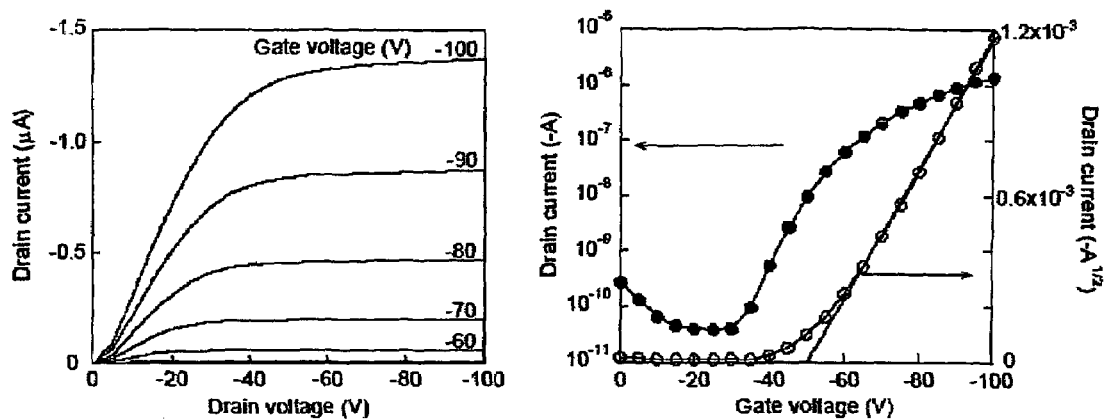
FIG. 9 is a drawing which illustrates characteristic curves of an organic thin film transistor in Examples of the present invention.
Figure 10:
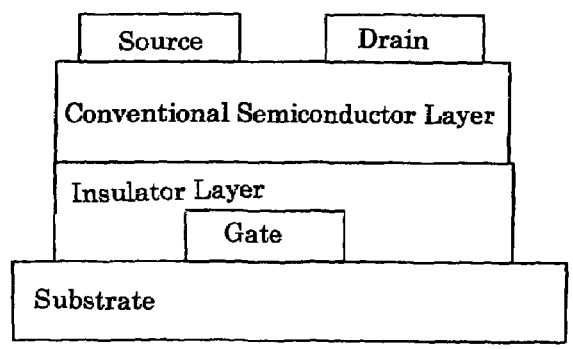
FIG. 10 is a drawing which illustrates a device structure of a typical conventional thin film transistor.

A gate voltage $V_G$ of −40 V was applied upon the gate electrode of the above organic thin film transistor and at the same time, a voltage was applied between the source and the drain resultantly feeding an electric current. In this situation, carriers are induced within a channel region (between the source electrode and the drain electrode) of the organic semiconductor layer, and the thin film transistor works as a p-type transistor. As a result, a transistor characteristic as shown in FIG. 9 was obtained. The On-Off ratio of the electric current between the source electrode and the drain electrode within an electric current saturation domain was $4 \times 10^4$. Further, an electric field-effect mobility μ of holes was calculated by a following equation (A) and as a result, it was $7 \times 10^{-3}$ cm²/Vs.

$$I_D = (W/2L)C\mu(V_G - V_T)^2 \qquad (A)$$

In the equation (A), $I_D$ represents an electric current between the source electrode and the drain electrode, W represents a channel width, L represents a channel length, C represents an electric capacitance per unit area of the gate insulator layer, $V_T$ represents a gate threshold voltage, and $V_G$ represents a gate voltage.

Examples 2 to 5

Organic thin film transistors were prepared in similar manners as Example 1 except that compounds described in Table 1 were employed instead of Compound (1). The prepared organic thin film transistors were driven as p-type transistors under the gate voltage $V_G$ of −40 V in the same manner as Example 1. On-Off ratios of the electric current between the source electrode and the drain electrode were measured together with calculating the electric field-effect mobility μ of holes. The results are shown in Table 1.

Examples 6 and 7

Organic semiconductor layers were formed in similar manners as Example 1 except that compounds described in Table 1 were employed as materials for the organic semiconductor layers instead of Compound (1). Subsequently, calcium (Ca) was vacuum vapor deposited as the source and the drain electrode through metal masking at a deposition rate of 0.05 nm/second instead of gold (Au) up to a thickness of 20 nm, followed by further vapor depositing silver (Ag) for covering calcium (Ca) at a deposition rate of 0.05 nm/second up to a thickness of 50 nm and as a result, organic thin film transistors were prepared. The prepared organic thin film transistors were driven as n-type transistors under the gate voltage $V_G$ of +40 V in the same manner as Example 1. On-Off ratios of the electric current between the source electrode and the drain electrode were measured together with calculating the electric field-effect mobility μ of electrons. The results are shown in Table 1.

Example 8

An organic thin film transistor was prepared in accordance with following steps. At first, a surface of a Si substrate (p-type; resistivity: 1 Ωcm; common use with a gate electrode) was oxidized in accordance with a thermal oxidation process, forming a thermal oxidation film having a thickness of 300 nm over the substrate and as a result, an insulator layer was provided. Further, after completely removing a $SiO_2$ film formed over another surface of the substrate by means of dry etching, a chromium film with a thickness of 20 nm was formed in accordance with a sputtering process, and further, a gold (Au) film with a thickness of 100 nm was formed in accordance with a sputtering process, resultantly taking out the films as an electrode. The substrate was ultrasonically cleaned with the use of neutral detergent, pure water, acetone and ethanol spending each 30 minutes respectively and after further cleaning with the use of ozone, a self-assembling monolayer of octadecyltrichlorosilane was formed.

Then, the substrate was set in a vacuum vapor deposition apparatus (EX-400; manufactured by ULVAC Co.) and the above Compound (2) was formed into a film of an organic semiconductor layer with a thickness of 50 nm at a vapor deposition rate of 0.05 nm/second over the insulator layer ($SiO_2$). Subsequently, a source electrode and a drain electrode separated with a distance (channel length: L) of 75 μm between each other without contacting each other were provided by forming a gold film having a thickness of 50 nm through metal masking. An organic thin film transistor having a width (channel width W) of 5 mm between the source electrode and the drain electrode was prepared (refer to FIG. 8).

The prepared organic thin film transistor was driven as p-type transistor under the gate voltage $V_G$ of −40 V in the same manner as Example 1. On-Off ratio of the electric current between the source electrode and the drain electrode was measured together with calculating the electric field-effect mobility μ of holes. The results are shown in Table 1.

Example 9

A source electrode and a drain electrode separated with a distance (channel length: L) of 75 μm between each other without contacting each other and having a width (channel width: W) of 5 mm were provided over a glass substrate having a thickness of 1 mm by forming a gold (Au) film having a thickness of 50 nm through metal masking. Subsequently, the foregoing Compound (2) was formed into an organic semiconductor layer having a film thickness of 50 nm in accordance with vacuum vapor deposition process through another metal masking and then, an insulator layer of parylene having a film thickness of 1 μm was formed in accordance with a thermal CVD process in a similar manner as Example 1. Finally, sputtering a gate electrode (Au) up to a thickness of 30 nm through another masking, an organic thin film transistor was prepared (refer to FIG. 1).

The prepared organic thin film transistor was driven as p-type transistor under the gate voltage $V_G$ of −40 V in the same manner as Example 1. On-Off ratio of the electric current between the source electrode and the drain electrode was measured together with calculating the field-effect mobility μ of holes. The results are shown in Table 1.

Example 10

Cleaning of the substrate, film-forming of the gate electrode and formation of the insulator layer were carried out in the same manner as Example 1. Subsequently, dissolving 3% by mass of the Compound (30) into toluene, the resultant solution was formed in accordance with a spin coating process to a film over the substrate after film-formation of the insulator layer, and the film was dried under an atmosphere of a nitrogen gas and at a temperature of 120° C. and as a result, an organic semiconductor layer was film-formed. Subsequently, a source electrode and a drain electrode separated without contacting each other were provided over the above film by forming a gold (Au) film having a thickness of 50 nm through metal masking with a use of vacuum vapor deposition apparatus resultantly preparing an organic thin film transistor. (refer to FIG. 3)

The prepared organic thin film transistor were driven as p-type transistor under the gate voltage $V_G$ of −40 V in the same manner as Example 1. On-Off ratio of the electric current between the source electrode and the drain electrode was measured together with calculating the electric field-effect mobility μ of holes. The results are shown in Table 1.

Comparative Example 1

An organic thin film transistor was prepared in the same manner as Example 10 except that polyparaphenylene vinylene (PPV) [molecular weight (Mn): 86000, molecular weight distribution (Mw/Mn=5.1)] was used instead of Compound (30).

The prepared organic thin film transistor was driven as p-type transistor under the gate voltage $V_G$ of −40 V in the same manner as Example 1. On-Off ratio of the electric current between the source electrode and the drain electrode was measured together with calculating the electric field-effect mobility μ of holes. The results are shown in Table 1.

Comparative Example 2

Employing polyparaphenylenevinylene (PPV) as a material for the organic semiconductor layer, steps until forming the organic semiconductor layer were conducted completely in the same manner as Comparative Example 1. Then, in the same manner as Example 6, calcium (Ca) was vacuum vapor deposited as the source and the drain electrode through metal masking, followed by further vapor depositing silver (Ag) for covering calcium (Ca) and as a result, an organic thin film transistor was prepared.

The prepared organic thin film transistor was driven as n-type transistor under the gate voltage $V_G$ of 40 V in the same manner as Example 6. On-Off ratio of the electric current between the source electrode and the drain electrode was measured together with calculating the electric field-effect mobility μ of electrons. The results are shown in Table 1.

TABLE 1

| Examples | Compound in the Organic Semiconductor Layer | Type of Transistor | Field-Effect Mobility ($cm^2/Vs$) | On/Off ratio |
| --- | --- | --- | --- | --- |
| 1 | (1) | p-type | $7 \times 10^{-3}$ | $4 \times 10^4$ |
| 2 | (2) | p-type | 0.13 | $6 \times 10^5$ |
| 3 | (40) | p-type | 0.2 | $5 \times 10^5$ |
| 4 | (43) | p-type | 0.028 | $1.2 \times 10^5$ |
| 5 | (92) | p-type | $6 \times 10^{-3}$ | $1 \times 10^5$ |
| 6 | (16) | n-type | 0.01 | $1 \times 10^5$ |
| 7 | (26) | n-type | 0.11 | $4 \times 10^5$ |
| 8 | (2) | p-type | 0.15 | $4 \times 10^5$ |
| 9 | (2) | p-type | 0.09 | $3 \times 10^5$ |
| 10 | (30) | p-type | 0.01 | $4 \times 10^3$ |
| Comparative Example 1 | PPV | p-type | $1 \times 10^{-5}$ | $1 \times 10^3$ |
| Comparative Example 2 | PPV | n-type | $1 \times 10^{-4}$ | $1 \times 10^3$ |

INDUSTRIAL APPLICABILITY

Exactly as explained above in detail, by employing the compound having a specified structure with high mobility as a material of the organic semiconductor layer, the organic thin film transistor of the present invention became to have a fast response speed (driving speed), and further, achieved a large On/Off ratio getting an enhanced performance as a transistor.

What is claimed is:

1. A thin film transistor comprising at least three terminals consisting of a gate electrode, a source electrode and a drain electrode; an insulator layer and an organic semiconductor layer on a substrate, which controls an electric current flowing between the source and the drain by applying an electric voltage across the gate electrode, wherein the organic semiconductor layer comprises a styryl compound represented by a following general formula (a):

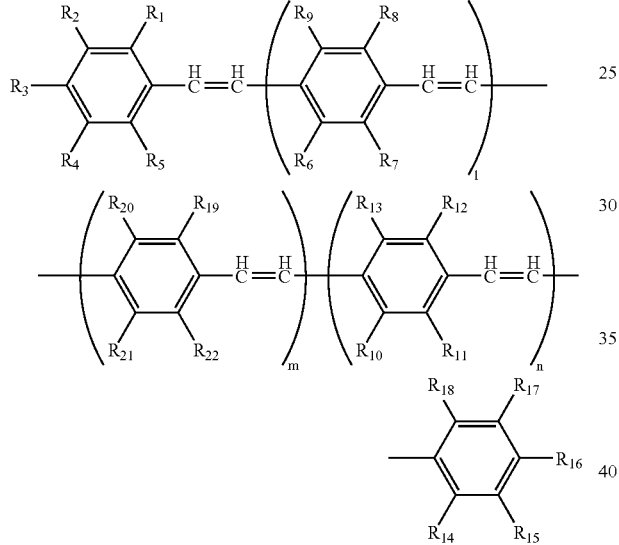

wherein $R_1$, $R_2$, $R_4$, $R_5$, $R_{14}$, $R_{15}$, $R_{17}$, and $R_{18}$ each independently represents a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, wherein alkyl groups of the dialkylamino group do not bond to each other, or bond to each other to form a ring structure containing a nitrogen atom, an alkylsulfonyl group having 1 to 30 carbon atoms, a haloalkylsulfonyl group having 1 to 30 carbon atoms, all of those have or do not have a substituent;

$R_3$ and $R_{16}$ represent the same groups and are a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, wherein alkyl groups of the dailkylamino group do not bond to each other, or bond to each other to form a ring structure containing a nitrogen atom, an alkylsulfonyl group having 1 to 30 carbon atoms, or a haloalkylsulfonyl group having 1 to 30 carbon atoms, all of those may have a substituent;

$R_6$ to $R_{13}$ each independently represents a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein alkyl groups of the dialkylamino group do not bond to each other, or bond to each other to form a ring structure containing a nitrogen atom, an alkylsulfonyl group having 1 to 30 carbon atoms, or a haloalkylsulfonyl group having 1 to 30 carbon atoms, all of those may have a substituent;

$R_{19}$ to $R_{22}$ each independently represents a hydrogen atom, a halogen a cyano group, an alkyl group having 1 to 6 carbon atoms, a haloalkyl group having 1 to 6 carbon atoms, an alkoxyl group having 1 to 6 carbon atoms, a haloakoxyl group having 1 to 6 carbon atoms, an alkylthio group having 1 to 6 carbon atoms, a haloalkylthio group having 1 to 6 carbon atoms, an alkylamino group having 1 to 6 carbon atoms, a dialkylamino group having 2 to 12 carbon atoms wherein alkyl groups of the dialkylamino group do not bond to each other, or bond to each other to form a ring structure containing a nitrogen atom, an alkylsulfonyl group having 1 to 6 carbon atoms, or a haloalkylsufonyl group having 1 to 6 carbon atoms, all of those may have a substituent; and l, m and n each represents an integer of 0 to 10; and a sum of l+m+n makes an integer of 2 to 20.

2. The organic thin film transistor according to Claim 1, wherein $R_1$, $R_2$, $R_4$, $R_5$, $R_6$, $R_7$, $R_8$, $R_9$, $R_{10}$, $R_{11}$, $R_{12}$, $R_{13}$, $R_{14}$, $R_{15}$, $_{17}$, and $R_{18}$ each independently represents a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein alkyl groups of the dailkylamino group do not bond to each other, or bond to each other to form a ring structure containing a nitrogen atom, an alkylsulfonyl group having 1 to 30 carbon atoms, or a haloalkylsulfonyl group having 1 to 30 carbon atoms, all of those have or do not have a substituent;

$R_3$ to $R_{16}$ represent the same groups a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein alkyl groups of the dialkylamino group do not bond to each other, or bond to each other to form a ring structure containing a nitrogen atom, an alkylsulfonyl group having 1 to 30 carbon atoms, or a haloalkylsulfonyl group having 1 to 30 carbon atoms, all of those have or do not have a substituent;

$R_{19}$ to $R_{22}$ each independently represents a hydrogen atom, a halogen atom, a cyano group, an alkyl group having 1 to 6 carbon atoms, a haloalkyl group having 1 to 6 carbon atoms, an alkxoyl group having 1 to 6 carbon atoms, a haloalkoxyl group having 1 to 6 carbon atoms, an alkylthio group having 1 to 6 carbon atoms, a haloalkylthio group having 1 to 6 carbon atoms, an alkylamino group having 1 to 6 carbon atoms, a dialkylamino group having 2 to 12 carbon atoms wherein alkyl groups of the dialkylamnio group do not bond to each other, or bond each to other to form a ring structure containing a nitrogen atom, an alkylsulfonyl group having 1 to 6 carbon atoms, or a haloalkylsufonyl group having 1 to 6 carbon atoms, all of those have or do not have a substituent; and l, m and n each represents an integer of 0 to 10; and a sum of l+m+n makes an integer of 2 to 20.

3. The organic thin film transistor according to claim 1, wherein $R_6$ to $R_{13}$ and $R_{19}$ to $R_{22}$ each independently represents a hydrogen atom, a halogen atom, a cyano group, an alkyl group having 1 to 6 carbon atoms, or a haloalkyl group having 1 to 6 carbon atoms.

4. The organic thin film transistor according to claim 1, wherein $R_3$ and $R_{16}$ each represent a hydrogen atom, a halogen atom, a cyano group, an alkyl group having 1 to 4 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms wherein alkyl groups of the dailkylamino group do not bond to each other, or bond to each other to form a ring structure containing a nitrogen atom, an alkylsulfonyl group having 1 to 30 carbon atoms, or a haloalkylsulfonyl group having 1 to 30 carbon atoms.

5. The organic thin film transistor according to claim 1, wherein $R_1$, $R_2$, $R_4$ to $R_{15}$ and $R_{17}$ to $R_{22}$ are all hydrogen atoms; each of $R_3$ or $R_{16}$ is an alkyl group having 1 to 3 carbon atoms, an alkoxyl group having 1 to 3 carbon atoms, or a hydrogen atom.

6. The organic thin film transistor according to claim 1, wherein any one of $R_1$ to $R_{22}$ represents a fluorine atom, a trifluoromethyl group or a pentafluoropropyl group, with the proviso that $R_3$ and $R_{16}$ represent the same groups.

7. The organic thin film transistor according to claim 1, wherein double bonds of a conjugated main chain of the styryl compound represented by the general formula (a) are disposed in trans position to each other.

8. The organic thin film transistor according to claim 1, wherein the styryl compound is represented by a following general formula (a'):

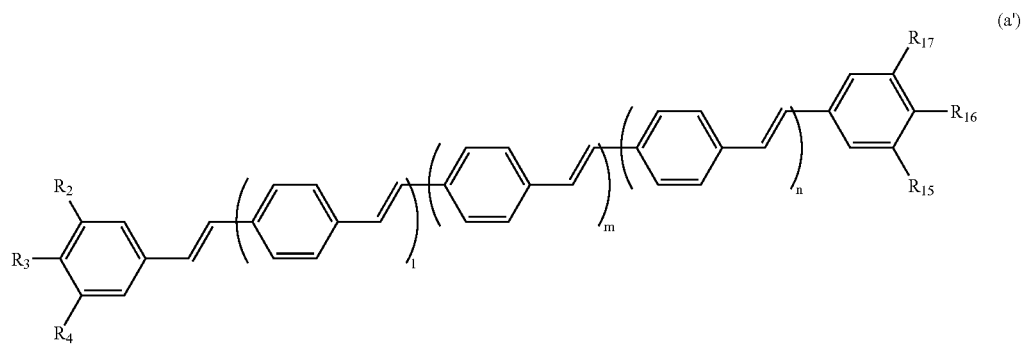

wherein $R_2$, $R_3$, $R_4$, $R_{15}$, $R_{16}$, and $R_{17}$ each independently represent a hydrogen atom, a halogen atom, a cyano group, an alkyl group having 1 to 30 carbon atoms, a haloalkyl group having 1 to 30 carbon atoms, an alkoxyl group having 1 to 30 carbon atoms, a haloalkoxyl group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms, wherein alkyl groups of the dialkylamino group do not bond to each other, or bond to each other to form a ring structure containing a nitrogen atom, an alkylsulfonyl group having 1 to 30 carbon atoms, or a haloalkylsulfonyl group having 1 to 30 carbon atoms, all of those have or do not have a substituent $R_2$ and $R_{15}$ represent the same groups;
$R_3$ and $R_{16}$ represent the same groups; and
$R_4$ and $R_{17}$ represent the same groups.

* * * * *